US011352620B2

(12) United States Patent
Siegers et al.

(10) Patent No.: US 11,352,620 B2
(45) Date of Patent: Jun. 7, 2022

(54) PEPTIDE LIBRARIES

(71) Applicant: MorphoSys AG, Planegg (DE)

(72) Inventors: Katja Siegers, Munich (DE); Jan Van Den Brulle, Munich (DE)

(73) Assignee: MORPHOSYS AG, Planegg (DE)

( * ) Notice: Subject to any disclaimer, the term of this patent is extended or adjusted under 35 U.S.C. 154(b) by 102 days.

(21) Appl. No.: 17/014,084

(22) Filed: Sep. 8, 2020

(65) Prior Publication Data

US 2020/0399630 A1 Dec. 24, 2020

Related U.S. Application Data

(63) Continuation of application No. 15/306,538, filed as application No. PCT/EP2015/059496 on Apr. 30, 2015, now Pat. No. 10,822,604.

(30) Foreign Application Priority Data

May 2, 2014 (EP) .................................... 14166898

(51) Int. Cl.
C12N 15/10 (2006.01)
G01N 33/68 (2006.01)
C07K 1/04 (2006.01)

(52) U.S. Cl.
CPC .......... *C12N 15/1037* (2013.01); *C07K 1/047* (2013.01); *G01N 33/6845* (2013.01)

(58) Field of Classification Search
None
See application file for complete search history.

(56) References Cited

U.S. PATENT DOCUMENTS

| 10,822,604 B2 | 11/2020 | Siegers et al. ..... C12N 15/1037 |
| 2002/0068301 A1 | 6/2002 | Lai et al. ........................ 435/7.1 |
| 2008/0313749 A1 | 12/2008 | Timmerman et al. ............ 800/3 |
| 2010/0317547 A1 | 12/2010 | Gregory et al. ................ 506/17 |

FOREIGN PATENT DOCUMENTS

| WO | 198403564 | 9/1984 |
| WO | 199309872 | 5/1993 |
| WO | 00/14536 | 3/2000 |
| WO | 200077194 | 12/2000 |
| WO | 2002031510 | 4/2002 |
| WO | 04/035735 | 4/2004 |
| WO | 2009098450 | 8/2009 |

OTHER PUBLICATIONS

Bedard et al. "A Convenient Approach to Prepare Topologically Segregated Bilayer Beads for One-Bead Two-Compound Combinatorial Peptide Libraries" Int J Pept Ther 2013 19:13-23.
Devlin et al. "Random Peptide Libraries: A Source of Specific Protein Binding Molecules" Science 1990 249:404-406.
Joo et al. "High-throughput Sequence Determination of Cyclic Peptide Library Members by Partial Edman Degradation/Mass Spectrometry" J Am Chem Soc 2005 128:13000-13009.
Landon et al. "Is Phage Display Technology on Target for Developing Peptide-Based Cancer Drugs?" Current Drug Discovery Technologies 2004 1:113-132.
Perosa et al. "Generation of biologically active linear and cyclic peptides has revealed a unique fine specificity of rituximab and its possible cross-reactivity with acid sphingomyelinase-like phosphodiesterase 3b precursor" Blood 2006 107 (3) :1070-1077.
Uchiyama et al. "Designing Scaffolds of Peptide for Phage Display Libraries" Journal of Bioscience and Bioengineering 99 (5) :448-456.
Van de Langemheen et al. "Scaffolded multiple cyclic peptide libraries for protein mimics by native chemical ligation" Org. Biol. Chem 2014 12:4471-4478.
International Search Report and Written Opinion in PCT/EP2015/059496 dated Sep. 10, 2015.
Extended European Search Report in Application No. 14166898.8 dated Oct. 14, 2014.
Ph.D™ Phage Display Libraries—Instruction Manual from New England Biolabs Oct. 2012.
Alessandro Angelini et al., "Bicyclic peptide inhibitor reveals large contact interface with a protease target", ACS Chemical Biology 2012 pp. 1-19.
Communication pursuant to Article 94(3) EPC in EP Application No. 15 720 692.1 dated Jan. 7, 2020.
Chen et al. "Bicyclic Peptide Ligands Pulled out of Cysteine-Rich Peptide Libraries" J. Am. Chem. Soc. 2013 135:6562-6569.
Matsubara et al. "A novel ICK peptide from the *Loxoceles intermedia* (brown spider) venom gland: Cloining, heterologous expression and immunological cross-reactivity approaches" Toxicon 2013 71:147-158.
Muller et al. "In Vitro Biosynthesis of the Prepeptide of Type-III Lantibiotic Labyrinthopeptin A2 Including Formation of a C—C Bond as a Post-translational Modiciation" Angew Chem Int Ed 2010 49:2436-2440.
Smith et al. "Small Binding Proteins Selection from a Combinatorial Repertoire of Knottins Displayed on Phage" J Mol Biol 1998 277:317-332.
Office Communication dated Jan. 3, 2020 in U.S. Appl. No. 15/306,538, filed Oct. 25, 2016.
Office Communication dated Jul. 1, 2020 in U.S. Appl. No. 15/306,538, filed Oct. 25, 2016.
Office Communication dated Jul. 8, 2020 in U.S. Appl. No. 15/306,538, filed Oct. 25, 2016.

*Primary Examiner* — Christopher M Gross
(74) *Attorney, Agent, or Firm* — Licata & Tyrrell P.C.

(57) ABSTRACT

The invention relates to novel libraries of linear and cyclic peptides, and methods of generating and screening such libraries for biological, pharmaceutical and other uses.

11 Claims, 19 Drawing Sheets

Specification includes a Sequence Listing.

FIG. 2A

| PeptideLibrary_L20 | ADEF GHIK LMN PQR STVW Y | ADEF GHIK LMN PQR STVW Y | ADEF GHIK LMN PQR STVW Y | ACDE FGHI KLM NPQ RSTV WY | ADEF GHIK LMN PQR STVW Y | ADEF GHIK LMN PQR STVW Y | ADEF GHIK LMN PQR STVW Y | ADEF GHIK LMN PQR STVW Y | ADEF GHIK LMN PQR STVW Y | ACDE FGHI KLM NPQ RSTV WY | ACDE FGHI KLM NPQ RSTV WY | ACDE FGHI KLM NPQ RSTV WY | ACDE FGHI KLM NPQ RSTV WY | ACDE FGHI KLM NPQ RSTV WY | ACDE FGHI KLM NPQ RSTV WY | ACDE FGHI KLM NPQ RSTV WY | ACDE FGHI KLM NPQ RSTV WY | ACDE FGHI KLM NPQ RSTV WY | ACDE FGHI KLM NPQ RSTV WY |
|---|---|---|---|---|---|---|---|---|---|---|---|---|---|---|---|---|---|---|---|
| A | 6 | 4 | 4 | 1 | 5 | 7 | 2 | 11 | 7 | 2 | 1 | 1 | 2 | 5 | 3 | 2 | 4 | 3 | 6 |
| C | | | | 52 | | | | | | 22 | 18 | 18 | 17 | 16 | 15 | 18 | 12 | 18 | 19 |
| D | 7 | 4 | 2 | 1 | 1 | 3 | 3 | 6 | 6 | 4 | 1 | 5 | 6 | 5 | 1 | 5 | 4 | 5 | 7 |
| E | 4 | 2 | 4 | 2 | 4 | 6 | 6 | 1 | 6 | 3 | 6 | 6 | 4 | 6 | 3 | 5 | 7 | 5 | 4 |
| F | 6 | 6 | 7 | | 5 | 2 | 4 | 6 | 5 | 4 | 4 | 1 | 2 | 1 | | 5 | 5 | 4 | 3 |
| G | 5 | 13 | 2 | 4 | 5 | 3 | 7 | 4 | 5 | 3 | 5 | 4 | 7 | 5 | 4 | 4 | 5 | 4 | 5 |
| H | 8 | 8 | 3 | 1 | 6 | 4 | 5 | 10 | 5 | 7 | 7 | 2 | 6 | 4 | 1 | 2 | 1 | 2 | 6 |
| I | 4 | 9 | 4 | 2 | 2 | 5 | 6 | 6 | 4 | 9 | 2 | 3 | 6 | 4 | 6 | 3 | 6 | 4 | 5 |
| K | 5 | 5 | 2 | | 1 | 2 | 2 | | 3 | 1 | 4 | 3 | 2 | 2 | 5 | 3 | 5 | 2 | |
| L | 3 | 3 | 2 | 4 | 6 | 10 | 3 | 5 | 7 | 6 | 3 | 11 | 6 | 8 | 8 | 4 | 2 | 3 | 5 |
| M | 5 | 2 | 7 | 7 | 6 | 4 | 6 | 4 | 7 | 1 | 5 | 6 | 11 | 4 | 5 | 3 | 7 | 5 | 3 |
| N | 4 | 3 | 5 | 2 | 5 | 3 | 4 | 3 | 3 | 2 | 3 | 3 | 4 | 3 | 2 | 4 | 3 | 8 | |
| P | 5 | 4 | 6 | 7 | 13 | 7 | 10 | 3 | 4 | 8 | 7 | 5 | 2 | 6 | 10 | | 4 | 6 | 10 |
| Q | 2 | 4 | 11 | 4 | 9 | 5 | 10 | 5 | 3 | 4 | 6 | 5 | 7 | 2 | 2 | 4 | 3 | 1 | 3 |
| R | 9 | 12 | 12 | 4 | 4 | 7 | 4 | 6 | 1 | 5 | 6 | 3 | 8 | 9 | 8 | 6 | 6 | 7 | 5 |
| S | 3 | 2 | 2 | 1 | 8 | 5 | 6 | 2 | 10 | 3 | 2 | 3 | | 5 | 6 | 3 | 5 | 3 | |
| T | 4 | 4 | 8 | 1 | 5 | 7 | 3 | 10 | 5 | 4 | 4 | 6 | 2 | 4 | 6 | 7 | 2 | 5 | 5 |
| V | 2 | 3 | 10 | 2 | 2 | 4 | 3 | 3 | 8 | 11 | 2 | 1 | 2 | 4 | 4 | 5 | 8 | 4 | 2 |
| W | 9 | 6 | 5 | 1 | 9 | 2 | 1 | 6 | 6 | 1 | 7 | 6 | 9 | 5 | 3 | 6 | 3 | 7 | 5 |
| Y | 8 | 5 | 3 | 3 | 3 | 7 | 7 | 8 | 4 | 3 | 3 | 5 | 1 | 3 | 8 | 3 | 7 | 4 | 3 |
| stop | | | | | | | | | | | | | | | | | | | |
| -1 | | | | | | | | | | | | | | | | | | | |
| ins | | | | | | | | | | | | | | | | | | | |
| additional errors | | | | | | | | | | | | | | | | | | 1 | |

FIG. 2B

Overview Amino Acid Distribution (Expectation %) (NGS Data)

| Peptide Library_L20 Expected | A | C | D | E | F | G | H | I | K | L | M | N | P | Q | R | S | T | V | W | Y |
|---|---|---|---|---|---|---|---|---|---|---|---|---|---|---|---|---|---|---|---|---|
| 1 | 5.3 | - | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 |
| 2 | 5.3 | - | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 |
| 3 | 5.3 | - | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 |
| 4 | 2.6 | 50 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 |
| 5 | 5.3 | - | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 |
| 6 | 5.3 | - | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 |
| 7 | 5.3 | - | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 |
| 8 | 5.3 | - | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 |
| 9 | 5.3 | - | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 |
| 10 | 5.3 | - | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 | 5.3 |
| 11 | 4.5 | 15 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| 12 | 4.5 | 15 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| 13 | 4.5 | 15 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| 14 | 4.5 | 15 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| 15 | 4.5 | 15 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| 16 | 4.5 | 15 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| 17 | 4.5 | 15 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| 18 | 4.5 | 15 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| 19 | 4.5 | 15 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| 20 | 4.5 | 15 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |

FIG. 2C

Overview Amino Acid Distribution (%) (NGS Data)

| Peptide Library_L20 Obtained | A | C | D | E | F | G | H | I | K | L | M | N | P | Q | R | S | T | V | W | Y |
|---|---|---|---|---|---|---|---|---|---|---|---|---|---|---|---|---|---|---|---|---|
| 1 | 5.7 | - | 5.1 | 4.4 | 5.2 | 6.8 | 5.5 | 5.7 | 3.8 | 4.2 | 5.9 | 5.8 | 4.4 | 3.7 | 8.2 | 5.8 | 4.6 | 3.6 | 4.9 | 6.4 |
| 2 | 5.4 | - | 4.6 | 4.5 | 4.7 | 7.2 | 4.7 | 4.8 | 4.4 | 4.4 | 6.7 | 4.7 | 5.5 | 5.4 | 8.4 | 5.3 | 4.6 | 3.4 | 6.1 | 5.0 |
| 3 | 6.7 | - | 5.9 | 4.5 | 3.1 | 7.3 | 4.2 | 4.1 | 4.3 | 4.3 | 7.1 | 4.0 | 6.1 | 5.5 | 8.7 | 5.4 | 4.4 | 3.6 | 6.1 | 4.5 |
| 4 | 1.5 | 48.8 | 3.0 | 2.8 | 1.7 | 3.7 | 2.4 | 2.5 | 1.8 | 3.1 | 4.9 | 2.0 | 3.0 | 3.2 | 4.1 | 1.4 | 2.1 | 2.4 | 3.5 | 2.2 |
| 5 | 4.2 | - | 4.7 | 5.4 | 2.7 | 7.7 | 7.7 | 4.3 | 2.1 | 7.2 | 7.8 | 4.7 | 7.3 | 4.7 | 8.2 | 4.6 | 6.2 | 3.0 | 5.2 | 2.2 |
| 6 | 6.3 | - | 4.4 | 6.6 | 4.1 | 4.8 | 5.9 | 5.0 | 2.7 | 5.9 | 6.3 | 3.9 | 5.6 | 5.2 | 5.7 | 4.6 | 7.4 | 4.5 | 6.1 | 5.2 |
| 7 | 7.2 | - | 4.6 | 6.1 | 4.6 | 5.2 | 4.9 | 5.3 | 2.6 | 5.7 | 5.5 | 4.5 | 5.1 | 4.2 | 5.6 | 5.0 | 7.7 | 4.9 | 5.9 | 5.3 |
| 8 | 6.8 | - | 4.1 | 5.9 | 4.8 | 5.5 | 5.1 | 5.5 | 2.4 | 5.5 | 5.4 | 4.4 | 6.0 | 4.1 | 6.0 | 5.1 | 7.6 | 5.0 | 5.8 | 5.1 |
| 9 | 7.9 | - | 5.2 | 6.0 | 4.2 | 5.2 | 4.5 | 4.9 | 3.2 | 4.9 | 6.4 | 4.4 | 4.8 | 4.0 | 5.0 | 5.0 | 7.0 | 5.6 | 6.7 | 4.9 |
| 10 | 5.1 | - | 3.8 | 5.0 | 1.8 | 10.9 | 5.3 | 3.1 | 0.7 | 7.3 | 6.2 | 4.3 | 13.1 | 3.3 | 10.4 | 4.0 | 6.2 | 1.1 | 6.1 | 2.5 |
| 11 | 2.4 | 18.6 | 4.6 | 3.5 | 3.2 | 5.1 | 6.2 | 4.3 | 3.0 | 4.3 | 5.3 | 3.4 | 5.9 | 5.2 | 7.5 | 3.4 | 3.2 | 2.6 | 4.3 | 3.8 |
| 12 | 3.3 | 16.7 | 5.1 | 3.6 | 3.3 | 5.2 | 5.6 | 3.9 | 3.5 | 5.0 | 5.9 | 3.7 | 5.0 | 4.8 | 7.3 | 3.9 | 3.5 | 3.3 | 4.1 | 3.5 |
| 13 | 3.5 | 15.6 | 4.8 | 3.3 | 2.8 | 5.3 | 5.7 | 4.3 | 3.2 | 5.3 | 5.9 | 3.3 | 5.0 | 5.6 | 7.4 | 4.3 | 3.3 | 3.8 | 3.7 | 4.0 |
| 14 | 3.6 | 15.4 | 4.7 | 4.6 | 2.6 | 5.3 | 5.7 | 4.7 | 2.9 | 5.7 | 6.5 | 2.8 | 4.7 | 4.9 | 6.7 | 3.9 | 3.6 | 4.1 | 4.5 | 3.3 |
| 15 | 2.7 | 16.3 | 4.1 | 4.4 | 1.9 | 4.8 | 4.9 | 3.4 | 2.0 | 5.4 | 5.5 | 3.9 | 6.6 | 4.1 | 9.7 | 4.4 | 5.5 | 3.5 | 4.7 | 2.1 |
| 16 | 2.9 | 13.6 | 3.3 | 5.5 | 2.2 | 4.0 | 3.9 | 4.6 | 3.6 | 5.6 | 5.2 | 3.6 | 5.8 | 5.3 | 6.4 | 3.6 | 7.0 | 4.8 | 5.2 | 3.9 |
| 17 | 2.9 | 15.2 | 3.0 | 5.0 | 2.6 | 4.6 | 3.5 | 5.0 | 3.6 | 4.8 | 5.0 | 3.9 | 5.3 | 4.2 | 5.9 | 3.9 | 6.4 | 5.1 | 5.0 | 5.0 |
| 18 | 2.9 | 15.6 | 3.6 | 5.1 | 2.6 | 4.6 | 4.1 | 4.1 | 2.9 | 4.3 | 5.3 | 3.5 | 5.6 | 4.3 | 6.9 | 3.3 | 6.6 | 5.0 | 5.4 | 4.5 |
| 19 | 2.7 | 16.8 | 3.4 | 5.3 | 2.9 | 3.9 | 3.7 | 3.8 | 4.0 | 4.4 | 4.9 | 3.3 | 5.3 | 4.6 | 6.2 | 3.0 | 5.8 | 5.6 | 5.6 | 4.8 |
| 20 | 2.7 | 20.6 | 5.2 | 3.3 | 4.9 | 4.4 | 7.0 | 5.0 | 1.8 | 4.8 | 4.5 | 3.9 | 5.0 | 3.1 | 5.7 | 2.7 | 3.0 | 2.7 | 2.9 | 6.7 |

Ring sizes in clones with 2 cysteine residues (NGS Data)

FIG. 5

Example Peptide resulting from Peptide Library_20:

| G | S | A | 1 | 2 | 3 | 4 | 5 | 6 | 7 | 8 | 9 | 10 | 11 | 12 | 13 | 14 | 15 | 16 | 17 | 18 | 19 | 20 | A | A | A |
|---|---|---|---|---|---|---|---|---|---|---|---|----|----|----|----|----|----|----|----|----|----|----|---|---|---|
| G | S | A | F | F | E | C | Q | I | S | H | W | L  | C  | V  | A  | W  | D  | L  | A  | E  | Y  | H  | A | A | A |
| G | S | A | N | G | P | C | G | F | E | F | G | A  | T  | E  | G  | L  | I  | S  | E  | Y  | C  | M  | A | A | A |
| G | S | A | Q | I | A | C | R | V | G | M | H | P  | I  | L  | Q  | Q  | F  | R  | Q  | T  | P  | C  | A | A | A |
| G | S | A | E | A | A | C | L | I | P | E | E | F  | M  | P  | C  | H  | N  | C  | V  | N  | P  | C  | A | A | A |
| G | S | A | A | R | D | C | P | L | P | D | F | N  | C  | G  | W  | C  | K  | C  | T  | M  | P  | P  | A | A | A |

FIG. 6

| | | | 1 | 2 | 3 | 4 | 5 | 6 | 7 | 8 | 9 | 10 | 11 | 12 | 13 | 14 | 15 | 16 | 17 | 18 | 19 | 20 | | | |
|---|---|---|---|---|---|---|---|---|---|---|---|---|---|---|---|---|---|---|---|---|---|---|---|---|---|
| G | S | A | Example Peptide resulting from Peptide Library_20 | | | | | | | | | | | | | | | | | | | | A | A | A |
| G | S | A | R | E | F | R | F | D | P | N | K | T | G | W | C | I | G | T | T | C | E | I | A | A | A |
| G | S | A | D | E | I | P | A | E | Q | L | I | P | V | N | D | M | C | Q | F | K | C | Q | A | A | A |
| G | S | A | D | Y | M | Q | E | H | N | E | V | S | D | Q | C | H | C | P | F | Q | F | D | A | A | A |
| G | S | A | E | H | F | R | M | S | M | L | T | G | M | C | L | P | C | T | R | W | C | | A | A | A |
| G | S | A | G | P | V | Q | L | V | P | E | V | N | C | S | M | C | P | N | Q | E | C | C | A | A | A | pIII Display Vector pVIII Display Vector

Expression Vector

FIG. 11

Sequences identified against Streptavidin

| X | X | X | X | X | X | X | X | X | X | X | X | X | X | X | X | X | X |
|---|---|---|---|---|---|---|---|---|---|---|---|---|---|---|---|---|---|
| A | P | Y | H | M | D | I | H | P | C | R | H | Q | Y | P | T | D | C |
| Y | D | D | C | P | M | N | P | S | Q | C | L | P | Q | F | G | E | S |
| P | I | V | K | H | - | F | D | P | F | D | D | H | P | Q | V | P | C |
| I | Q | P | P | H | T | V | W | D | G | R | C | V | H | L | H | Q | G |
| G | R | D | D | M | Q | F | N | G | M | C | L | N | L | D | A | R | N |
| N | P | H | D | W | A | N | E | S | Q | C | H | M | Q | F | E | C | K |
| H | A | F | S | E | T | D | Z | L | P | A | H | P | Q | F | G | C | N |
| D | R | S | V | S | E | K | N | E | P | H | H | P | A | Q | E | K | C |
| K | N | W | G | V | S | N | H | D | C | H | C | H | D | E | G | H | E |
| R | M | G | E | P | P | G | M | F | C | H | P | M | R | D | C | T | N |
| A | E | W | E | D | D | T | K | D | N | M | P | Q | V | E | M | R | D |
| R | M | G | E | M | H | G | F | F | C | C | P | Q | R | D | C | T | N |
| V | G | D | M | T | D | G | G | L | P | H | G | M | C | E | Q | D | P |
| S | D | P | D | H | Q | S | L | A | Y | C | Y | W | G | S | V | D | C |
| N | P | E | T | N | Q | Q | M | H | P | C | P | M | E | P | E | K | C |
| A | E | A | F | W | A | D | N | T | P | K | F | C | H | D | N | R | N |
| H | W | H | V | G | R | D | N | L | P | C | L | P | Y | F | E | C | T |
| G | A | V | C | E | G | D | G | R | Q | C | R | D | S | R | T | - | Q |
| E | P | N | N | P | Q | P | G | T | P | M | T | P | P | R | K | Q | N |
| P | F | Q | C | E | Q | N | E | P | Q | H | P | E | F | V | D | P | Y |
| F | W | K | E | P | Q | F | G | Q | Q | Q | E | G | R | E | C | K | P |
| G | R | E | C | W | Q | F | P | T | D | S | V | V | E | G | D | W | R |
| A | V | G | D | S | Q | G | P | H | D | M | H | L | L | L | S | D | R |

FIG. 12

Sequences identified against anti-C-myc antibody

SEQUENCE LISTING

```
<160> NUMBER OF SEQ ID NOS: 64

<210> SEQ ID NO 1
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(10)
<223> OTHER INFORMATION: a, c, t, g, unknown or other

<400> SEQUENCE: 1 ctcttcnnnn                                                          10

<210> SEQ ID NO 2
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(4)
<223> OTHER INFORMATION: a, c, t, g, unknown or other

<400> SEQUENCE: 2 nnnngagacg                                                          10

<210> SEQ ID NO 3
<211> LENGTH: 13
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: modified_base
<222> LOCATION: (1)..(7)
<223> OTHER INFORMATION: a, c, t, g, unknown or other

<400> SEQUENCE: 3
nnnnnnngaa gag                                                          13

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(14)
<223> OTHER INFORMATION: a, c, t, g, unknown or other

<400> SEQUENCE: 4
ctcttcnnnn nnnngagacg                                                   20

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(14)
<223> OTHER INFORMATION: a, c, t, g, unknown or other

<400> SEQUENCE: 5
cgtctcnnnn nnnngaagag                                                   20

<210> SEQ ID NO 6
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(6)
<223> OTHER INFORMATION: Any of the twenty standard, naturally occurring
      amino acids, except Cys
<220> FEATURE:
<221> NAME/KEY: MOD_RES
<222> LOCATION: (7)..(7)
<223> OTHER INFORMATION: Any of the twenty standard, naturally occurring
      amino acids
<220> FEATURE:
<221> NAME/KEY: MOD_RES
<222> LOCATION: (8)..(13)
<223> OTHER INFORMATION: Any of the twenty standard, naturally occurring
      amino acids, except Cys
<220> FEATURE:
<221> NAME/KEY: MOD_RES
<222> LOCATION: (14)..(23)
<223> OTHER INFORMATION: Any of the twenty standard, naturally occurring
      amino acids

<400> SEQUENCE: 6
```

Gly Ser Ala Xaa Xaa Xaa Xaa Xaa Xaa Xaa Xaa Xaa Xaa Xaa Xaa
1               5                   10                  15

Xaa Xaa Xaa Xaa Xaa Xaa Xaa Ala Ala Ala
            20                  25

<210> SEQ ID NO 7
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Ser Ala Phe Phe Glu Cys Gln Ile Ser His Trp Leu Cys Val Ala
1               5                   10                  15

Trp Asp Leu Ala Glu Tyr His Ala Ala Ala
            20                  25

<210> SEQ ID NO 8
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Ser Ala Asn Gly Pro Cys Gly Phe Glu Phe Gly Ala Thr Glu Gly
1               5                   10                  15

Leu Ile Ser Glu Tyr Cys Met Ala Ala Ala
            20                  25

<210> SEQ ID NO 9
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Ser Ala Gln Ile Ala Cys Arg Val Gly Met His Pro Ile Leu Gln
1               5                   10                  15

Gln Phe Arg Gln Thr Pro Cys Ala Ala Ala
            20                  25

<210> SEQ ID NO 10
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Ser Ala Glu Ala Ala Cys Leu Ile Pro Glu Glu Phe Met Pro Cys
1               5                   10                  15

His Asn Cys Val Asn Pro Cys Ala Ala Ala
            20                  25

```
<210> SEQ ID NO 11
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Ser Ala Ala Arg Asp Cys Pro Leu Pro Asp Phe Asn Cys Gly Gly
1               5                   10                  15

Trp Cys Lys Cys Thr Met Pro Ala Ala Ala
            20                  25

<210> SEQ ID NO 12
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Ser Ala Arg Glu Phe Arg Phe Asp Pro Asn Lys Thr Gly Trp Cys
1               5                   10                  15

Ile Gly Thr Thr Cys Glu Ile Ala Ala Ala
            20                  25

<210> SEQ ID NO 13
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gly Ser Ala Asp Glu Ile Pro Ala Glu Gln Leu Ile Pro Val Asn Asp
1               5                   10                  15

Met Cys Gln Phe Lys Cys Gln Ala Ala Ala
            20                  25

<210> SEQ ID NO 14
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Ser Ala Asp Tyr Met Gln Glu His Asn Glu Val Ser Asp Gln Cys
1               5                   10                  15

His Cys Pro Phe Gln Phe Asp Ala Ala Ala
            20                  25

<210> SEQ ID NO 15
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
```

```
        Synthetic peptide"

<400> SEQUENCE: 15

Gly Ser Ala Glu His Phe Arg Met Ser Met Leu Thr Gly Met Cys Leu
1               5                   10                  15

Pro Cys Cys Thr Arg Trp Cys Ala Ala Ala
            20                  25

<210> SEQ ID NO 16
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Ser Ala Gly Pro Val Gln Leu Val Pro Glu Val Asn Cys Ser Met
1               5                   10                  15

Cys Pro Asn Gln Glu Cys Cys Ala Ala Ala
            20                  25

<210> SEQ ID NO 17
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis"

<400> SEQUENCE: 17

His His His His His His
1               5

<210> SEQ ID NO 18
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ala Pro Tyr His Pro Met Asp Ile His Pro Cys Arg His Pro Gln Tyr
1               5                   10                  15

Pro Thr Asp Cys
            20

<210> SEQ ID NO 19
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Tyr Asp Asp Cys His Pro Met Asn Pro Ser Gln Cys Leu Pro Pro Gln
1               5                   10                  15

Phe Gly Glu Ser
            20
```

```
<210> SEQ ID NO 20
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Pro Ile Val Lys Tyr Ile Thr Phe Asp Pro Phe Asp Asp Cys His Pro
1               5                   10                  15

Gln Val Pro Cys
            20

<210> SEQ ID NO 21
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ile Gln Pro Cys His Pro Gln Val Trp Asp Gly Arg Cys Asn Val Leu
1               5                   10                  15

Asn His Gln Gly
            20

<210> SEQ ID NO 22
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Arg Asp Cys His Pro Gln Phe Asn Gly Met Cys Leu Met Leu Asp
1               5                   10                  15

Arg Ala Arg Asn
            20

<210> SEQ ID NO 23
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asn Pro His Asp Met Thr Ala Asn Glu Ser Gln Cys His Pro Gln Phe
1               5                   10                  15

Gly Ala Cys Lys
            20

<210> SEQ ID NO 24
<211> LENGTH: 20
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 24

His Ala Phe Ser Trp Glu Gln Asp Asn Leu Pro Cys His Pro Gln Phe
1               5                   10                  15

Gly Glu Cys Asn
            20

<210> SEQ ID NO 25
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Asp Arg Ser Val Glu Ser Asp Lys His Glu Pro Ala Cys His Pro Gln
1               5                   10                  15

Tyr Gly Lys Cys
            20

<210> SEQ ID NO 26
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Lys Asn Trp Gly Val Pro Met Asn Met Asp Cys His Pro Met Cys Ala
1               5                   10                  15

Lys Cys His Glu
            20

<210> SEQ ID NO 27
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Arg Met Gly Glu Ile Asp Gly Lys Phe Cys His Pro Gln Arg Asp
1               5                   10                  15

Lys Cys Thr Asn
            20

<210> SEQ ID NO 28
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ala Glu Trp Glu Thr His Asp Thr Phe Asp Asn His Pro Gln Val Glu
1               5                   10                  15
```

```
Glu Met Arg Asp
            20

<210> SEQ ID NO 29
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Arg Met Gly Glu Ile Asp Gly Gly Lys Phe Cys His Pro Gln Arg Asp
1               5                   10                  15

Lys Cys Thr Asn
            20

<210> SEQ ID NO 30
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Val Gly Glu Cys His Pro Gln Gly Gly Leu Pro Met Gly Met Cys Glu
1               5                   10                  15

Tyr Gln Asp Pro
            20

<210> SEQ ID NO 31
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ser Asp Met Cys His Pro Gln Ser Gly Ala Tyr Cys Tyr Trp Pro Ser
1               5                   10                  15

His Val Asp Cys
            20

<210> SEQ ID NO 32
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Asn Pro Asp Met Pro Ala Arg Thr Leu His Cys His Pro Met Gly Ser
1               5                   10                  15

Arg Glu Lys Cys
            20

<210> SEQ ID NO 33
<211> LENGTH: 20
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ala Glu Thr Pro Gly Trp Gly Gln Met Thr Pro Met Phe Cys His Pro
1               5                   10                  15

Gln Asn Arg Cys
            20

<210> SEQ ID NO 34
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

His Ala Phe Ser Trp Glu Gln Asp Asn Leu Pro Cys His Pro Gln Phe
1               5                   10                  15

Gly Glu Cys Asn
            20

<210> SEQ ID NO 35
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (19)..(19)
<223> OTHER INFORMATION: Any amino acid

<400> SEQUENCE: 35

Gly Trp Val Cys His Pro Gln Asp Asn Arg Cys Ile Glu Asp Arg Arg
1               5                   10                  15

Lys Thr Xaa Thr
            20

<210> SEQ ID NO 36
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Glu Pro Asn Val Met Pro Asn Pro Trp Thr Lys Cys His Pro Met Arg
1               5                   10                  15

Asp Lys Cys Gln
            20

<210> SEQ ID NO 37
<211> LENGTH: 20
<212> TYPE: PRT
<213> ORGANISM: Artificial Sequence
<220> FEATURE:
```

-continued

```
<221> NAME/KEY: source
<223> OTHER INFORMATION: /note="Description of Artificial Sequence:
      Synthetic peptide"

<400> SEQUENCE: 37

Pro Phe Gln Cys His Pro Gln Asn Gly Pro Cys Met Tyr Glu Ala Val
1               5                   10                  15

Pro Lys Pro Asn
            20

<210> SEQ ID NO 38
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Phe Trp Lys Cys His Pro Gln Phe Gly Gln Cys His Glu Gly Met Glu
1               5                   10                  15

Gly Asp Lys Tyr
            20

<210> SEQ ID NO 39
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gly Arg Glu Cys His Pro Gln Phe Glu Thr Asp Gln Ser Val Leu Gly
1               5                   10                  15

Gln Cys Trp Pro
            20

<210> SEQ ID NO 40
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Ala Val Gly Asp His Pro Gln Gly Pro His Asp Ser Met His Leu Leu
1               5                   10                  15

Glu Ser Asp Arg
            20

<210> SEQ ID NO 41
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Trp Ala Leu Cys Asn Asn Thr Gly Leu Gln Gln Cys Leu Ile Pro Glu
```

```
1               5                   10                  15

Met Asp Leu Asp
            20

<210> SEQ ID NO 42
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ile Val Gly Trp Gly Gly Lys Leu Ile Ser Glu His Glu His Cys Asn
1               5                   10                  15

Thr Val Phe Asp
            20

<210> SEQ ID NO 43
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ile Glu Ile Cys Ser Arg Asp Arg Asp Pro Ser Leu Ile Pro Glu Tyr
1               5                   10                  15

Cys Met Met Arg
            20

<210> SEQ ID NO 44
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Met Gln Trp Trp Gln Glu Ala Tyr Ser Thr Asn Ser Gln Gln Arg Cys
1               5                   10                  15

His Cys Met Arg
            20

<210> SEQ ID NO 45
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Trp Lys Gln Cys Asn Ile Ser Gly Ala Ile Asp Leu Ile Ser Glu Glu
1               5                   10                  15

Cys Met Gly Leu
            20

<210> SEQ ID NO 46
```

```
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Asn Gln Lys Cys Pro Lys Gly Asp Val Ser Gln Cys Leu Ile Ala Glu
1               5                   10                  15

Glu Glu Met Ile
            20

<210> SEQ ID NO 47
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Pro Gly Asn Val Val Leu Val Pro Glu Ala Cys Met His Gln Glu Tyr
1               5                   10                  15

Thr Thr Gly Cys
            20

<210> SEQ ID NO 48
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Ser Tyr Leu Ile Pro Glu Glu Met His Ile Cys Asn Ile Ser Asp
1               5                   10                  15

Met Ala Ser Cys
            20

<210> SEQ ID NO 49
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Arg Thr Cys Asn Phe Asn Gly Glu Met Gly Leu Ile Ser Glu Ser
1               5                   10                  15

Cys Met His Trp
            20

<210> SEQ ID NO 50
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 50

Trp Gly Ser Cys Leu Ile Pro Glu Glu Ser Ile Gly Gln Arg Glu Pro
1               5                   10                  15

Thr Gln Cys Asp
            20

<210> SEQ ID NO 51
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gln Ile His Cys Ile Arg Glu Gln Glu Ser Glu Tyr Leu Ile Pro Glu
1               5                   10                  15

Asp Cys Leu Glu
            20

<210> SEQ ID NO 52
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Arg Glu Trp Cys Asn Tyr Ser Asn Trp Pro Val Gln Leu Ile Pro Glu
1               5                   10                  15

Lys Cys Met His
            20

<210> SEQ ID NO 53
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Asn Gly Pro Cys Gly Phe Glu Phe Gly Ala Thr Glu Gly Leu Ile Ser
1               5                   10                  15

Glu Tyr Cys Met
            20

<210> SEQ ID NO 54
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Lys Glu Thr Cys Leu Ile Pro Glu Ala Ala Met Asn Leu Arg Met Ala
1               5                   10                  15

His Glu Val Cys
```

-continued

```
                20

<210> SEQ ID NO 55
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Glu Ala Ala Cys Leu Ile Pro Glu Glu Phe Met Pro Cys His Asn Cys
1               5                   10                  15

Val Asn Pro Cys
            20

<210> SEQ ID NO 56
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gln Pro Thr Cys Pro Glu Ile Arg Gln Pro Gly Leu Ile Ser Glu Trp
1               5                   10                  15

Cys Met Glu Ser
            20

<210> SEQ ID NO 57
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Leu Asp Phe Cys His Thr Met Thr Trp Ser His Gly Leu Cys Pro Arg
1               5                   10                  15

Leu Val Ser Glu
            20

<210> SEQ ID NO 58
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gln Pro Ala Cys Ile His Phe Glu Lys Leu Arg Leu Ile Ser Glu Tyr
1               5                   10                  15

Glu Met Ser Cys
            20

<210> SEQ ID NO 59
<211> LENGTH: 20
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 59

Gly Pro Val Gln Leu Val Pro Glu Val Asn Cys Ser Met Cys Pro Asn
1               5                   10                  15

Gln Glu Cys Cys
            20

<210> SEQ ID NO 60
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Ala Asp Asn Cys Glu Ala Asn Gln Ala Arg Gly Cys Leu Ile Pro Glu
1               5                   10                  15

Glu Tyr Met His
            20

<210> SEQ ID NO 61
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ile Glu Ala Cys Gly Val Asn Gly Glu Arg Thr Cys Tyr Leu Ile Ser
1               5                   10                  15

Glu Glu Glu Met
            20

<210> SEQ ID NO 62
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ile Glu Ala Cys Gly Val Asn Gly Glu Arg Thr Cys Tyr Leu Ile Ser
1               5                   10                  15

Glu Glu Glu Met
            20

<210> SEQ ID NO 63
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63
```

```
Arg Tyr Asn Cys Gly Val Glu Gly Lys Ser Gln Leu Val Ser Glu Tyr
1               5                   10                  15

Cys Val Glu Lys
            20

<210> SEQ ID NO 64
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Ile Glu Ala Cys Gly Val Asn Gly Glu Arg Thr Cys Tyr Leu Ile Ser
1               5                   10                  15

Glu Glu Glu Met
            20
```

PEPTIDE LIBRARIES

This patent application is a continuation of U.S. Ser. No. 15/306,538 filed Oct. 25, 2016 which is the National Stage of International Application No. PCT/EP2015/059496 filed Apr. 30, 2015, which claims the benefit of priority from European Application No. 14166898.8, filed May 2, 2014, each of which are herein incorporated by reference in their entirety.

SEQUENCE LISTING

The instant application contains a Sequence Listing which is in ASCII format and is hereby incorporated by reference in its entirety. Said ASCII copy, created on May 30, 2014, is named MS212PCTSL.txt and is 23,198 bytes in size.

FIELD OF THE INVENTION

The invention relates to novel libraries containing both linear and cyclic peptides, and methods of generating and screening such libraries for biological, pharmaceutical and other uses.

BACKGROUND OF THE INVENTION

Peptide libraries have many uses. Such libraries can be used to identify therapeutically relevant molecules, or can serve other purposes, such as, the epitope mapping and characterization of therapeutically relevant molecules.

Therapeutically, peptides have certain advantages over small molecules and large molecule inhibitors, such as, antibodies. As compared to small molecules, peptides typically have a larger interface with an antigen, which interface comprises hydrogen bonds and van der Waals forces. This leads to high binding affinities, a high specificity for the antigen and typically a high potency. As compared to antibodies, peptides are much smaller and therefore typically penetrate tissue more easily. Certain tumors are inaccessible for antibody therapy. Different peptides may be used in libraries. Linear peptides, for example, at times have certain disadvantages. They are highly flexible and do not typically adopt unique, reproducible conformations. The lack of fixed structure reduces the affinity a peptide might have for an antigen and makes determination of the active conformation of the peptide extremely difficult. In addition, linear peptides are more easily susceptible to proteases, therefore, may be degraded in the human body.

As a result, strategies have been described to introduce constraints into peptides. Constrained peptides have much higher reproducible conformations and are generally more resistant to proteases. Peptides which are presented in a constrained manner may be generated by various means. For example, cyclic peptides may be utilized, e.g. cyclic peptides which are formed by disulfide bonds.

A complementary method for peptide library based lead discovery is the display of libraries on filamentous bacteriophages. This method allows the preparation of libraries as large as $10^{10}$ unique peptide members, many orders of magnitude larger than libraries that may be prepared synthetically. In addition to large library sizes, advantages of phage display include ease of library construction, coupling of the binding entity (displayed peptide) to a unique identifier (its DNA sequence), a selection protocol for amplifying binding clones in a pool, and the high fidelity of biosynthesis (compared to synthetic methods). Furthermore, rapid and inexpensive selection protocols are available for identifying those library members that bind to a target of interest.

Additionally, libraries displaying constrained, for example, cyclic, peptides can be distinguished based upon whether they display large single loop peptides, e.g. having cyclic structures, or peptides having multiple smaller loops. Large single loop libraries have the advantage of presenting many different conformations. While multiple, smaller loop libraries offer more constrained peptides with reproducible conformations, and peptides having multiple binding sites may have higher binding affinity and specificity than single larger loop peptides.

Multiple research groups have provided libraries having either linear peptides or cyclic peptides, but not libraries having both. Most commonly the length of the randomized peptides ranges between 5 and 16 amino acids.

New England Biolabs provides the Ph.D™ Phage Display Libraries. Two of these libraries are libraries of randomized linear peptides having either 7 or 12 amino acids in length. Other libraries of this system comprise fixed length cyclic peptides, each having an N and C terminal cysteine residue. Cyclic structures are formed via the disulfide bonds between the cysteine residues.

Bicycle Therapeutics provides a phage display peptide library having randomized constrained peptides of 16 amino acids in length. The peptides comprise three fixed cysteine residues at positions 2, 9, 16. The constrained structure is formed via a bond between a cysteine residue and a chemical moiety, thus resulting in each member having two fixed length randomized loops (see WO2009098450).

Genentech describes phage display libraries of fixed length randomized cyclic peptides where each member has an N and C terminal cysteine which form a disulfide bond (see WO200077194). These libraries each have different fixed lengths, the different libraries ranging from 5-16 amino acids.

Additionally, epitope mapping technologies are known which utilize libraries of linear peptides. These peptides are tested with the binding molecule of interest thereby allowing the determination of linear epitopes (see Pepscan WO 84/03564 and WO 93/09872). The a target protein of interest is split into a set of overlapping linear oligopeptides, which are separately produced and immobilized by chemical synthesis on solid support systems. The use of such target-specific custom made peptide libraries is, however, a rather cost and labor/time intensive process which is limited to linear peptide sequences and, therefore, does not allow the identification of conformational epitopes.

Libraries of randomized cyclic peptides which are fixed to a solid support and which may be used for epitope mapping are also described (see Pepscan WO2002031510). Sang Hoon Joo et al., High Throughput Sequence Determination of Cyclic Peptide Library Members by Partial Edman Degradation/Mass Spectrometry, J. Am. Chem. Soc. (2006) 128, 13000-13009 describes libraries of chemically synthesized peptides which displayed cyclic peptides on beads, where a percentage of the beads presented were linear due to cyclization failure, where the displayed cyclic peptides had only a single loop.

Bedard et al., A Convenient Approach to Prepare Topologically Segregated Bilayer Beads for One-Bead Two-Compound Combinatorial Peptide Libraries, Int. J. Pept. Res. Ther. (2013) 19:13-23 13009 describes libraries of chemically synthesized peptides which displayed cyclic peptides on beads, where a percentage of the beads presented were linear due to cyclization failure, where the displayed cyclic peptides had only a single loop.

Fumiaki Uchiyama et al., Designing Scaffolds of Peptides for Phage Display Libraries, Journal of Bioscience and Bioengineering (2005) Vol. 99, No. 5, 448-456 describes libraries of cyclic peptides having one fixed loop length and only a single loop.

Perosa et al., Generation of biologically active linear and cyclic peptides has revealed a unique fine specificity of rituximab and its possible cross-reactivity with acid sphingomyelinase-like phosphodiesterase 3b precursor, Blood (2006) 107:3, 1070-1077 discloses a phage display peptide library expressing a 7-mer cyclic (c7c) library having one fixed loop length and only a single loop.

Many of the known libraries generate the randomization of amino acids using degenerate oligonucleotides (NNN and NNK technology). This, however, may result in the generation of unwanted stop codons, or undesired motifs, such as protease cleavage sites or restriction sites.

Multiple approaches exist, but it is clear, that there is a high need to advance the utility of peptide phage display libraries for the use in identifying and/or characterizing therapeutically relevant molecules and other purposes, such as epitopes mapping.

SUMMARY OF THE INVENTION

Many of the aforementioned shortcomings are solved by the peptide libraries of the present disclosure. The peptide libraries of the present disclosure comprise linear and cyclic, constrained peptides, wherein in embodiments the ratio of cyclic to linear peptides can be specifically designed. Preferably, said peptide libraries are phage display libraries.

In an aspect, the peptides are translated from nucleic acids.

Such libraries can be used to identify therapeutically relevant and therapeutically active molecules, or can be used to characterize such molecules by means, such as, epitope mapping.

In many cases it is advantageous to present structurally constrained, for example, cyclic, peptides as well as linear peptides in one library.

In addition, there is utility in a library comprising constrained, for example, cyclic, peptides having a range of different loop lengths. Such libraries comprise a wide range of conformations.

In addition, there is utility in screening a library comprising constrained, for example, cyclic, peptides where some members have single loops and other members have multiple loops. Such libraries further comprise a wider range of conformations. With the currently available peptide libraries the simultaneous presentation of a) linear and cyclic peptides, b) constrained peptides having a range of different loop lengths, and c) constrained peptides having one or two or more loops is not feasible. As a result, screening experiments must be done by alternative or successive screenings using two or more different libraries, which is laborious.

The disclosed library, however, incorporates a) linear and cyclic peptides, b) constrained, for example, cyclic, peptides having a range of different loop lengths, and c) constrained, for example, cyclic, peptides having one or two or more loops.

In a state of the art linear randomized peptide library, depending upon the length of the peptides, a small percentage of molecules may have at least two cysteine molecules, forming a small percentage of constrained peptides. This is however a random process and the libraries have a different composition than those disclosed herein.

The libraries of the present disclosure have utility in both situations, i.e. in situations where either a linear or constrained peptide are sought in one screening.

In aspects, the library is designed to have a predictable proportion of both linear and constrained peptides. The present disclosure provides such a design as specific positions are selected to encode either a cysteine residue or other amino acid, wherein the ratio selected enables a higher proportion of constrained, for example, cyclic, peptides to be displayed and expressed as compared to the known randomized linear peptide libraries.

The presently described libraries allow for a very broad diversity, as compared to the state of the art. The state of the art linear peptides are known to often fail to maintain reproducible conformations. The state of the art cyclic peptides are formed by N and C terminal disulfide bonds, with fixed length cyclic regions, which also limits the diversity of conformations presented.

By controlling the ratio of cysteines at various positions, the present disclosure provides peptide libraries having a high diversity of conformations useful in many situations. The library presents both linear, and constrained, for example, cyclic peptides, where the peptides have multiple different loop lengths of disulfide bond formed (cyclic) loops ranging from, e.g., 3-17 amino acids in length, thus allowing for a large diversity of conformations being presented. In addition, such design produces peptides having 0, 1, 2 or more cysteines, allowing for the production of peptides having even more than one or two loops, thus further diversifying the conformations presented even more.

Accordingly, the libraries comprise (a) linear and cyclic peptides, (b) cyclic peptides having different loop lengths, and (c) cyclic peptides having two or more loops. This allows for the presentation of both linear and cyclic peptides in one screening. As, the libraries comprise peptides having different loop lengths, a wide variety of conformations can be displayed in one screening. And, as the libraries comprise peptides having two or more loops, further conformations can be displayed in one screening. Such a diversified library is not yet known, and for the first time provides all of the above features in one library where one screening can be used to more quickly identify important molecules.

In addition, the state of the art teaches small peptides ranging from 5-16 amino acids in length. The present disclosure in certain embodiments provides libraries of peptides of 15 amino acids or more in length.

An embodiment of the present disclosure provides a peptide library, wherein each member of the library comprises an amino acid sequence Cmix-(X) m-(Amix) n, wherein
  a) Cmix is a mixture of 50% cysteine and an equal mixture of the remaining natural occurring amino acids,
  b) X are each an equal mixture of the natural occurring amino acids, excluding cysteine,
  c) Amix are each a mixture of 5-50% cysteine and an equal mixture of the remaining natural occurring amino acids, and
  d) m and n are both, and independently from each other, 3-20.

In embodiments of the present disclosure, the natural occurring amino acids are selected from A, C, D, E, F, G, H, I, K, L, M, N, P, Q, R, S, T, V, W, and Y.

An embodiment of the present disclosure provides a peptide library as shown in FIG. 1.

In certain embodiments the peptide libraries of the present disclosure are displayed on bacteriophage. Phage display is known to have significant advantages in allowing the rapid selection of useful molecules. This method allows the preparation of libraries as large as $10^{10}$ unique peptide members, many orders of magnitude larger than libraries that may be prepared synthetically. Using such a robust platform allows for the display of large, diverse libraries.

Certain embodiments of the present disclosure provide the nucleic acids encoding the peptide libraries of the present disclosure. The present disclosure also provides vectors comprising the nucleic acids encoding the peptide library the present disclosure. In certain embodiments, the vector is a display vector. In other embodiments, the vector is an expression vector.

Embodiments of the present disclosure provide methods of identifying a peptide specific for an antigen, comprising contacting an antigen with the peptide library of the present invention, and selecting one or more peptides specific for said antigen.

Embodiments of the present disclosure also provide the peptides identified using the peptide libraries of the present invention.

DESCRIPTION OF THE DRAWINGS

FIGS. 2A, 2B and 2C show a quality assessment of the peptide library of FIG. 1. This figure shows the position and distribution of each amino acid, including the cysteines, which form the cyclic peptides disclosed herein. Therefore, this figure shows that the design of FIG. 1 successfully produces a library with the desired positions and distributions of cysteine residues. FIG. 2A shows the amino acid distribution of 99 individually sampled clones using Sanger sequencing. FIG. 2B shows the expected amino acid distribution. FIG. 2C shows the actual amino acid distribution as evaluated using Next Generation Sequencing.

FIG. 3A shows the evaluation of 99 individually sampled clones using Sanger sequencing. On average, 2.27 cysteines were identified per clone. Of the 99 clones sampled, 33% were linear and 67% were cyclic. FIG. 3B shows an evaluation using Next Generation Sequencing. FIG. 3C shows the expected versus obtained cysteines per clone as evaluated using Next Generation Sequencing.

FIG. 4A shows the evaluation of 99 individually sampled clones using Sanger sequencing. FIG. 4B shows the ring sizes as evaluated using Next Generation Sequencing. The cyclic peptides comprised loops ranging in size from 3-17 amino acids in length.

FIG. 5 shows an example of peptides (SEQ ID NO:s 7-11, respectively) in order of appearance, expressed from a library of FIG. 1. These examples have at least two cysteines and some even four cysteines per peptide, which result in various sized loops and even multiple loops within one peptide.

FIG. 6 shows and example of peptides (SEQ ID NO:s 12-16, respectively) in order of appearance) expressed from the library of FIG. 1. These examples have at least two cysteines and some even four cysteines per peptide, which result in various sized loops and even multiple loops within one peptide.

FIG. 11 shows the sequencing results of peptides (SEQ ID NO:s 18-40, respectively, in order of appearance) identified in a screening with the peptide library of FIG. 1 against streptavidin. This result confirms the utility of the library of FIG. 1 as a tool for epitope mapping. The results confirm that the known epitope of streptavidin, HPQ, was to a high confidence level identified in both linear and cyclic peptides.

FIG. 12 shows the sequencing results of peptides (SEQ ID NO:s 41-64, respectively, in order of appearance) identified in a screening with the peptide library of FIG. 1 against the anti-c-Myc antibody. This result confirms that a diverse number of specific peptides can be identified, wherein the peptides selected are both linear, constrained, and have a wide range of confirmations.

DEFINITIONS

Figure 1:
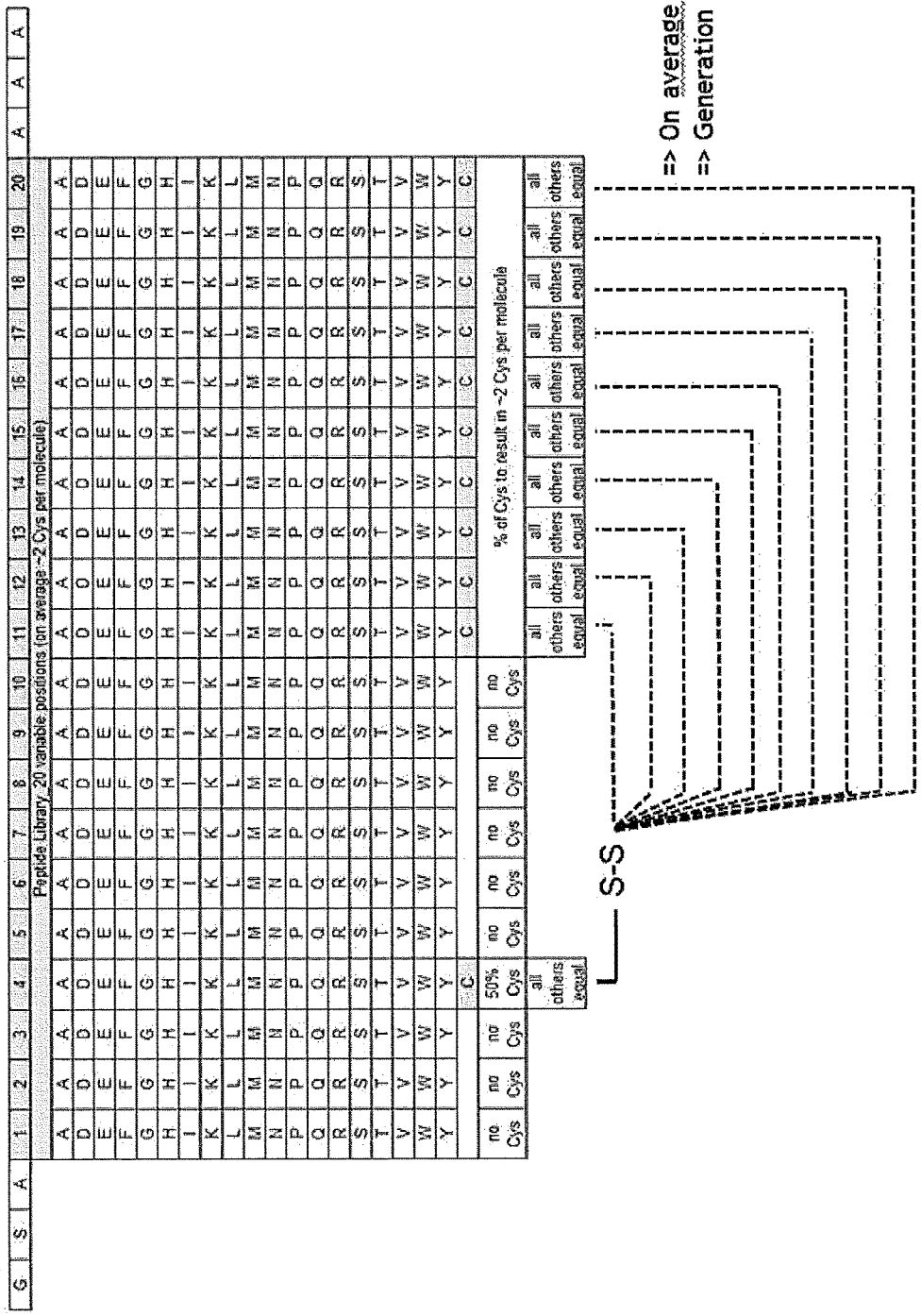
FIG. 1 shows a design of a peptide library disclosed herein which expresses a peptide library according to the present disclosure. (SEQ ID NO: 6.)

"Library" means an entity comprising more than one member. In the context of the present disclosure this term refers to a library of peptides, wherein said library comprises at least two different peptides.

"Synthetic" means not physically derived from naturally occurring DNA.

"Peptide" means a molecule having less than or equal to 50 amino acids.

Peptides "translated from nucleic acids" means peptides that are created using biological processes where the starting material is a nucleic acid, either DNA or RNA and the resulting material are amino acids. The biological process may include intermediary steps, such as transcription from DNA to RNA, and/or translation from RNA to amino acid. Such libraries displaying peptides translated from nucleic acids could be bacteriophage or ribosomal display libraries.

"Linear" as used in the present disclosure refers to a stretch of amino acids or a peptide that does not include any circular structure.

"Cyclic" or "circular" or "loop" as used in the present disclosure refers to a stretch of amino acids or a peptide which includes a circular structure. Not the entire stretch of amino acids or peptide needs to be circular. Cyclic peptides may be formed by covalent or by non-covalent bonds.

A typical covalent bond that is utilized within the present disclosure to form cyclic peptides is a disulfide bond, which is formed between two cysteine residues of the peptide. Other covalent bonds that are used within the present disclosure are thioether bonds, such as the thioether bonds which are formed and/or which are present in lanthionines. In vivo lanthionines are formed enzymatically via the dehydration of serine or threonine to yield dehydroalanine and dehydrobutyrine, respectively. These products then react with cysteine thiol to from lanthionine and methyllanthionine, respectively. Chemical synthesis is possible as well.

Other covalent bonds include lysinoalanine linkage between a dehydrated serine to yield dehydroalanine which alkylates a lysine in the same polypeptide.

Non-covalent bonds that are used within the present disclosure to from cyclic peptides are typically formed via protein domains, such as zinc-finger domains, a jun-fos interaction or a leucine zipper. Other non-covalent bonds may be used as well, such as hydrogen bonds, dipolar bonds or van der Waals forces.

"Constrained" as used in the present disclosure refers to a peptide in which the three-dimensional structure is maintained substantially in one spatial arrangement over time. The cyclic peptides within the present disclosure have a constrained conformation.

Methods of determining whether peptides are constrained are known in the art. For cyclic peptides this can in certain cases be deduced from the analysis of the primary amino acid sequence, for example, by the identification of cysteines. Another way is the addition of a protease to the displayed peptide library. Conformationally constrained peptides are usually not cut by the protease. Reduction in size after cleavage can be detected using mass spectrometry. Finally, mass spectrometry can also be used to analyze the library as such. Many cyclic peptides, especially those that are formed by dehydration, will have a lower mass than the corresponding linear peptides.

"Member" is one molecule forming part of a library. In the context of the present disclosure this term refers to one peptide which is part of the peptide library.

"Equal mixture" means that each codon encoding an amino acid has the same probability of occurring as any other codon encoding a different amino acid. As an example, if X1 represents an equal mixture of the naturally occurring amino acids, then each of the 20 naturally occurring amino acids has the same probability of occurring at that position, i.e. 5%.

"Natural occurring amino acids" means the following amino acids:

| Amino acid | Three letter code | One letter code |
|---|---|---|
| Alanine | Ala | A |
| Arginine | Arg | R |
| asparagine | Asn | N |
| aspartic acid | Asp | D |
| Cysteine | Cys | C |
| glutamic acid | Glu | E |
| glutamine | Gln | Q |
| Glycine | Gly | G |
| Histidine | His | H |
| isoleucine | Ile | I |
| Leucine | Leu | L |
| Lysine | Lys | K |
| methionine | Met | M |
| phenylalanine | Phe | F |
| Proline | Pro | P |
| Serine | Ser | S |
| threonine | Thr | T |
| tryptophan | Trp | W |
| Tyrosine | Tyr | Y |
| Valine | Val | V |

The term "vector" refers to a polynucleotide molecule capable of transporting another polynucleotide to which it has been linked. Preferred vectors are those capable of autonomous replication and/or expression of nucleic acids to which they are linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and mammalian vectors). Other vectors can be integrated into the genome of a host cell upon introduction into the host cell, and thereby are replicated along with the host genome. Vectors may be compatible with prokaryotic or eukaryotic cells. Prokaryotic vectors typically include a prokaryotic replicon which may include a prokaryotic promoter capable of directing the expression (transcription and translation) of the peptide in a bacterial host cell, such as Escherichia coli transformed therewith. A promoter is an expression control element formed by a DNA sequence that permits binding of RNA polymerase and transcription to occur. Promoter sequences compatible with bacterial hosts are typically provided in plasmid vectors containing convenience restriction sites for insertion of a DNA segment. Examples of such vector plasmids include pUC8, pUC9, pBR322, and pBR329, pPL and pKK223, available commercially.

"Expression vectors" are those vectors capable of directing the expression of nucleic acids to which they are operatively linked and is intended to include such other forms of expression vectors, such as viral vectors (e.g., replication defective retroviruses, adenoviruses and adeno-associated viruses), which serve equivalent functions.

"Display vector" includes a DNA sequence having the ability to direct replication and maintenance of the recombinant DNA molecule extra chromosomally in a host cell, such as a bacterial host cell, transformed therewith. Such DNA sequences are well known in the art. Display vectors can for example be phage vectors or phagemid vectors originating from the class of fd, M13, or fl filamentous bacteriophage. Such vectors are capable of facilitating the display of a protein including, for example, a binding protein or a fragment thereof, on the surface of a filamentous bacteriophage. Display vectors suitable for display on phage, ribosomes, DNA, bacterial cells or eukaryotic cells, for example yeast or mammalian cells are also known in the art, for example, as are viral vectors or vectors encoding chimeric proteins.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Typical host cells are prokaryotic (such as bacterial, including but not limited to E. coli) or eukaryotic (which includes yeast, mammalian cells, and more). Bacterial cells are preferred prokaryotic host cells and typically are a strain of Escherichia coli (E. coli) such as, for example, the E. coli strain DH5 available from Bethesda Research Laboratories, Inc., Bethesda, Md. Preferred eukaryotic host cells include yeast and mammalian cells including murine and rodents, preferably vertebrate cells such as those from a mouse, rat, monkey or human cell line, for example HKB11 cells, PERC.6 cells, or CHO cells.

The introduction of vectors into host cells may be accomplished by a number of transformation or transfection methods known to those skilled in the art, including calcium phosphate precipitation, electroporation, microinjection, liposome fusion, RBC ghost fusion, protoplast fusion, viral infection and the like. The production of monoclonal full-length antibodies, Fab fragments, Fv fragments and scFv fragments is well known.

Transformation of appropriate cell hosts with a recombinant DNA molecule is accomplished by methods that typically depend on the type of vector and cells used. With regard to transformation of prokaryotic host cells, see, for example, Cohen et al., Proceedings National Academy of Science, USA, Vol. 69, P. 2110 (1972); and Maniatis et al., Molecular Cloning, a Laboratory Manual, Cold spring Harbor Laboratory, Cold Spring Harbor, N.Y. (1982). With regard to the transformation of vertebrate cells with retroviral vectors containing rDNAs, see for example, Sorge et al., Mol. Cell. Biol., 4:1730-1737 (1984); Graham et al., Virol., 52:456 (1973); and Wigler et al., Proceedings National Academy of Sciences, USA, Vol. 76, P. 1373-1376 (1979).

The term "epitope" refers to an antigenic determinant, i.e. the part of an antigen that is recognized by a binding molecule, such as an antibody or a peptide. "Phage display" is a technique by which variant polypeptides are displayed as fusion proteins to a coat protein on the surface of phage, e g filamentous phage particles. A utility of phage display lies in the fact that large libraries of randomized protein variants can be rapidly and efficiently sorted for those sequences that bind to a target molecule with high affinity display of peptides and proteins libraries on phage has been used for screening millions of polypeptides for ones with specific binding properties. Polyvalent phage display methods have been used for displaying small random peptides and small proteins through fusions to either gene III or gene VIII of filamentous phage Wells and Lowman (1992) Curr Opin Struct Biol B 355-362 and references cited therein. In monovalent phage display, a protein or peptide library is fused to a gene III or a portion thereof and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations Lowman and Wells (1991) Methods A companion to Methods in Enzymology 3205-216. In phage display, the phenotype of the phage particle, including the displayed polypeptide corresponds to the genotype inside the phage particle, the DNA enclosed by the phage coat proteins.

Phage display describes a selection technique in which a library of peptide or protein variants is expressed on the outside of a phage virion, while the genetic material encoding each variant resides on the inside. This creates a physical linkage between each variant protein sequence and the DNA encoding it, which allows rapid partitioning based on binding affinity to a given target molecule (antibodies, enzymes, cell-surface receptors, etc.) by an in vitro selection process called panning. In its simplest form, panning is carried out by incubating a library of phage-displayed peptides on a plate (or bead) coated with the target, washing away the unbound phage, and eluting the specifically bound phage. The eluted phage are then amplified and taken through additional binding/amplification cycles to enrich the pool in favor of binding sequences. After a few rounds, individual clones are characterized by DNA sequencing and ELISA.

A "phagemid" is a plasmid vector having a bacterial origin of replication, e.g., ColE 1, and a copy of an intergenic region of a bacteriophage. The phagemid may be based on any known bacteriophage including filamentous bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles This term includes phagemids which contain a phage coat protein gene or fragment thereof linked to a heterologous polypeptide gene as a gene fusion such that the heterologous polypeptide is displayed on the surface of the phage particle Sambrook et. al. 417.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as, an M 13 fl. fd, Pf3 phage or a derivative thereof, a lambdoid phage. such as lambda, 21, phi80, phi81. 82, 424. 434, etc, or a derivative thereof, a Baculovirus or a derivative thereof, a T4 phage or a derivative thereof, a T7 phage virus or a derivative thereof. Preparation of DNA from cells means isolating the plasmid DNA from a culture of the host cells. Commonly used methods for DNA preparation are the large- and small-scale plasmid preparations described in sections 125-133 of in Sambrook et al. After preparation of the DNA it can be purified by methods well known in the art such as that described in section 140 of Sambrook et. al.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell. The coat protein may be the major coat protein or may be a minor coat protein. A "major" coat protein is a coat protein which is present in the viral coat at 10 copies of the protein or more, e.g. major coat protein pVIII. A major coat protein may be present in tens, hundreds or even thousands of copies per virion. A minor coat protein is present in the viral coat at less than 10 copies per phage, e.g. minor coat protein pIII.

A "fusion protein" is a polypeptide having two portions covalently linked together, where each of the portions is a polypeptide having a different property The property may be a biological property, such as activity in vitro or in vivo The property may also be a simple chemical or physical property, such as binding to a target molecule, catalysis of a reaction, etc. The two portions may be linked directly by a single peptide bond or through a peptide linker containing one or more ammo acid residues Generally, the two portions and the linker will be in reading frame with each other "Polymerase chain reaction" or "PCR" refers to a procedure or technique in which minute amounts of a specific piece of nucleic acid. RNA and/or DNA. are amplified as described in U.S. Pat. No. 4,683,195 issued 28 Jul. 1987 Generally, sequence information from the ends of the region of interest or beyond needs to be available, such that ohgonucleotide primers can be designed, these primers will be identical or similar in sequence to opposite strands of the template to be amplified The 5' terminal nucleotides of the two primers may coincide with the ends of the amplified material PCR can be used to amplify specific RNA sequences, specific DNA sequences from total genomic DNA, and cDNA transcribed from total cellular RNA, bacteriophage or plasmid sequences, etc See generally Mullis et al (1907) Cold Spring Harbor S\mp Quant Biol 51 263, Erlich. ed. PCR Technology (Stockton Press, N Y, 1989) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid

DETAILED DESCRIPTION OF THE INVENTION

The present disclosure is directed to peptide libraries comprising constrained peptides and linear peptides. The present disclosure is directed to peptide libraries comprising cyclic peptides and linear peptides. Such libraries are useful for numerous purposes, including epitope mapping and the identification of peptides with pharmaceutical properties, such as anti-microbial or anti-viral peptides, material-specific peptides, small molecule binders, novel enzyme substrates and other peptides useful for drug lead discovery.

In order for a library to have utility in both situations where either a linear or constrained, for example, cyclic, peptide is sought, a library may be designed to have a predictable proportion of both linear and constrained, for example, cyclic, peptides presented. In certain embodiments, the peptide libraries comprise linear and cyclic peptides, wherein the cyclic peptides are formed by one or more covalent or one or more non-covalent bonds.

In certain embodiments, the covalent bond is a disulfide bond or a bond between two non-naturally occurring amino acids, such as, a thioether bond. In certain embodiments, the thioether bond is a lanthiopeptide, such as a lanthiopeptide formed between a dehydrated serine and a cysteine or a dehydrated threonine and a cysteine.

Figure 3A:
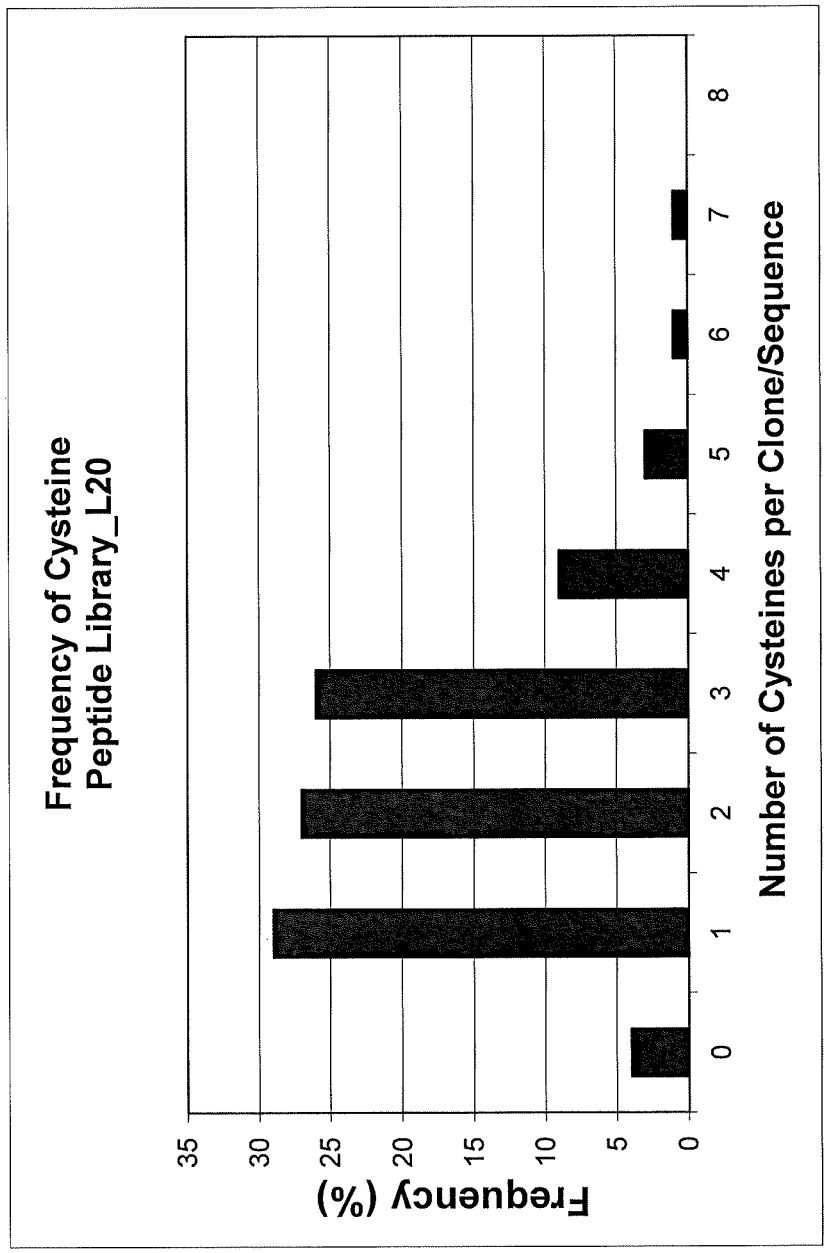
FIGS. 3A, 3B and 3C show how the peptide library of FIG. 1 expresses clones having 0, 1, 2 or more cysteine residues.

In certain embodiments, the covalent bond is a disulfide bond. In certain embodiments, the disulfide bond is formed by two cysteine residues. In certain embodiments, the library comprises peptides comprising 0, 1, 2, 3, 4, 5, 6 or 7 or more cysteine residues. In certain embodiments, the library comprises peptides comprising 0, 1, 2, 3, 4, 5, 6 and 7 cysteine residues. FIG. 3A shows the sequencing results of a peptide library of the present disclosure which comprises peptides having 0, 1, 2, 3, 4, 5, 6 or 7 cysteines per peptide. In certain embodiments, the library comprises peptides comprising 0, 1, 2, 3 or more cysteine residues. In certain embodiments, the library comprises peptides comprising 0, 1, 2, and 3 cysteine residues. In certain embodiments, the library comprises peptides comprising 0, 1, 2, 3, 4 or more cysteine residues. In certain embodiments, the library comprises peptides comprising 0, 1, 2, 3 and 4 cysteine residues. In certain embodiments, the library comprises peptides comprising 0, 1, 2, 3, 4, 5 or more cysteine residues. In certain embodiments, the library comprises peptides comprising 0, 1, 2, 3, 4 and 5 cysteine residues. In certain embodiments, the library comprises peptides comprising 0, 1, 2, 3, 4, 5, 6 or more cysteine residues. In certain embodiments, the library comprises peptides comprising 0, 1, 2, 3, 4, 5 and 6 cysteine residues.

In certain embodiments, the covalent bond is a lysinoalanine linkage formed between a dehydrated serine and a lysine.

In certain embodiments, the non-covalent bond is a formed via a protein domain, such as, a zinc-finger domain, a jun-fos interaction or a leucine zipper.

In an aspect, the disclosed library incorporates a) linear and cyclic peptides, b) constrained and non-constrained peptides, c) cyclic peptides having a range of different loop lengths, and d) cyclic peptides having one or two or more loops.

In an aspect, a library of peptides comprises (a) linear and cyclic peptides, (b) cyclic peptides having different loop lengths, and (c) cyclic peptides having two or more loops. In embodiments, the library comprises synthetic peptides. In embodiments, the library comprises peptides translated from nucleic acids.

Figure 4A:
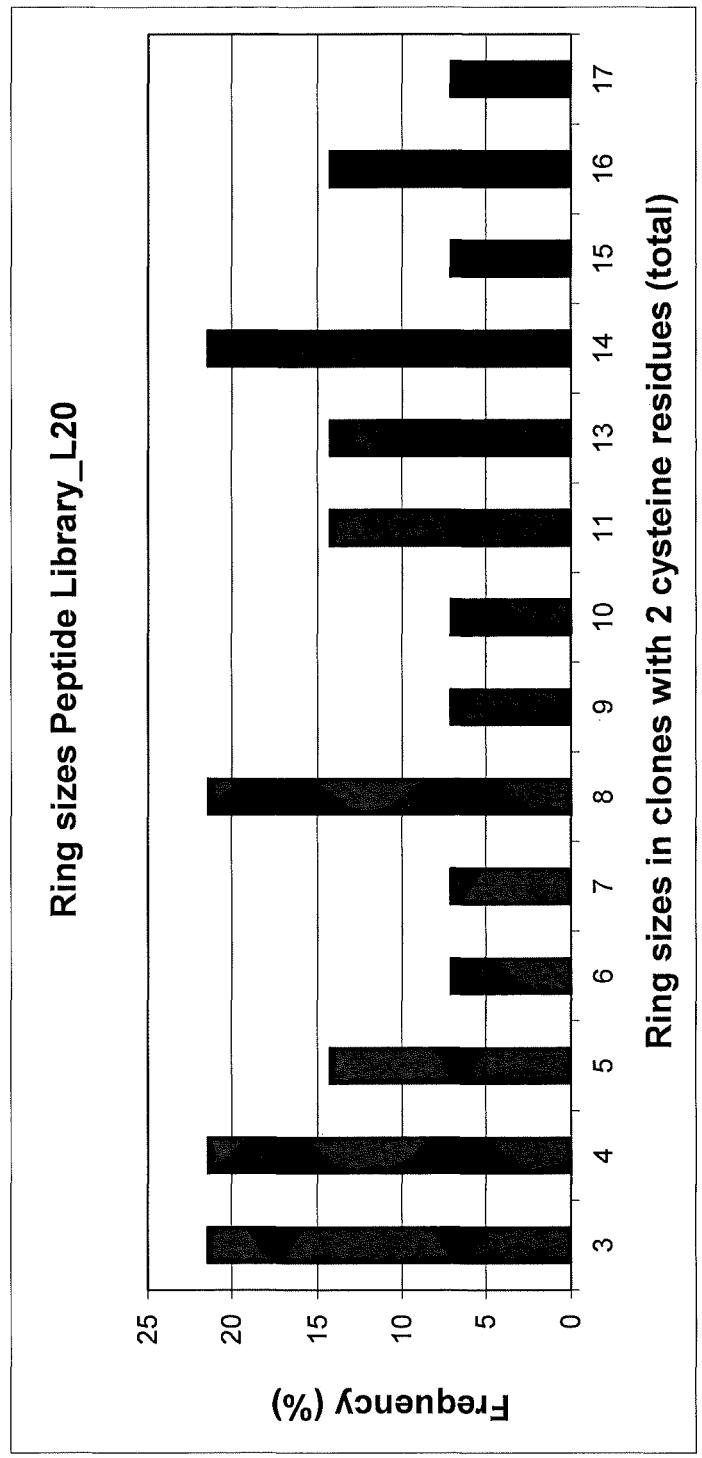
FIGS. 4A and 4B show how the peptide library of FIG. 1 expresses clones having at least two cysteines, thus forming cyclic structures, and the length distribution of ring sizes.
Figure 4B:
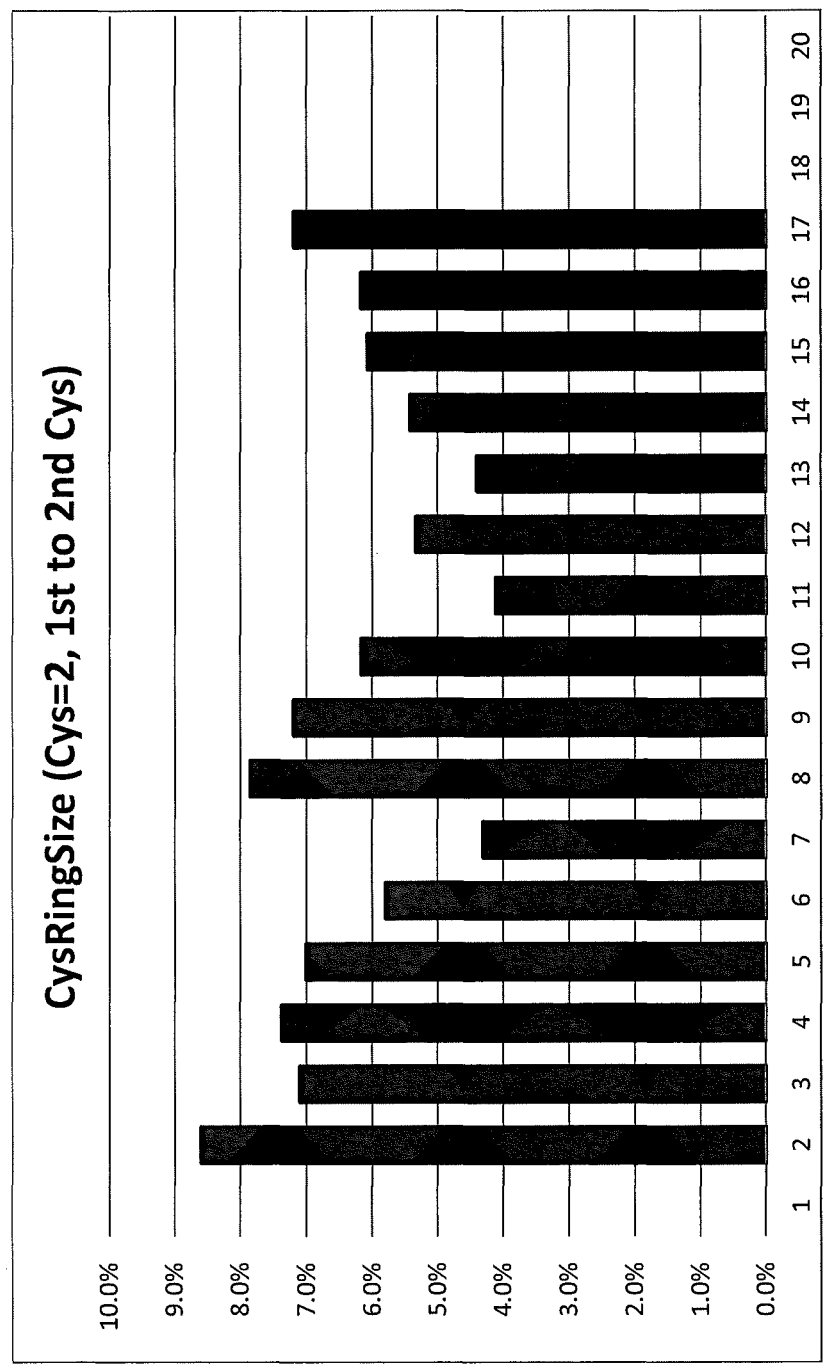

In embodiments, the library comprises cyclic peptides with loop lengths ranging from 3-17 amino acids in length. In embodiments, the library comprises cyclic peptides comprising loop lengths of 3, 4, 5, 6, 7, 8, 9, 10, 11, 12, 13, 14, 15, 16, or 17 amino acids. In embodiments, the library comprises cyclic peptides comprising loop lengths of 3, 4, 5, 6, 7, 8, 9, 10, 11, 12, 13, 14, 15, 16, and 17 amino acids. FIGS. 4A and 4B shows the sequencing results of a peptide library of the present disclosure which comprises peptides having comprising loop lengths of 3, 4, 5, 6, 7, 8, 9, 10, 11, 12, 13, 14, 15, 16, or 17 amino acids. In embodiments, the library comprises cyclic peptides comprising loop lengths of 3, or 4, or more amino acids. In embodiments, the library comprises cyclic peptides comprising loop lengths of 3, and 4 amino acids. In embodiments, the library comprises cyclic peptides comprising loop lengths of 3, 4, 5 or more amino acids. In embodiments, the library comprises cyclic peptides comprising loop lengths of 3, 4 and 5 amino acids. In embodiments, the library comprises cyclic peptides comprising loop lengths of 3, 4, 5, 6 or more amino acids. In embodiments, the library comprises cyclic peptides comprising loop lengths of 3, 4, 5 and 6 amino acids. In embodiments, the library comprises cyclic peptides comprising loop lengths of 3, 4, 5, 6, 7 or more amino acids. In embodiments, the library comprises cyclic peptides comprising loop lengths of 3, 4, 5, 6 and 7 amino acids. In embodiments, the library comprises cyclic peptides comprising loop lengths of 3, 4, 5, 6, 7, 8 or more amino acids. In embodiments, the library comprises cyclic peptides comprising loop lengths of 3, 4, 5, 6, 7 and 8 amino acids. In embodiments, the library comprises cyclic peptides comprising loop lengths of 3, 4, 5, 6, 7, 8, 9 or more amino acids. In embodiments, the library comprises cyclic peptides comprising loop lengths of 3, 4, 5, 6, 7, 8 and 9 amino acids. In embodiments, the library comprises cyclic peptides comprising loop lengths of 3, 4, 5, 6, 7, 8, 9, 10 or more amino acids. In embodiments, the library comprises cyclic peptides comprising loop lengths of 3, 4, 5, 6, 7, 8, 9 and 10 amino acids. In embodiments, the library comprises cyclic peptides comprising loop lengths of 3, 4, 5, 6, 7, 8, 9, 10, 11 or more amino acids. In embodiments, the library comprises cyclic peptides comprising loop lengths of 3, 4, 5, 6, 7, 8, 9, 10 and 11 amino acids. In embodiments, the library comprises cyclic peptides comprising loop lengths of 3, 4, 5, 6, 7, 8, 9, 10, 11, 12 or more amino acids. In embodiments, the library comprises cyclic peptides comprising loop lengths of 3, 4, 5, 6, 7, 8, 9, 10, 11 and 12 amino acids. In embodiments, the library comprises cyclic peptides comprising loop lengths of 3, 4, 5, 6, 7, 8, 9, 10, 11, 12, 13 or more amino acids. In embodiments, the library comprises cyclic peptides comprising loop lengths of 3, 4, 5, 6, 7, 8, 9, 10, 11, 12 and 13 amino acids. In embodiments, the library comprises cyclic peptides comprising loop lengths of 3, 4, 5, 6, 7, 8, 9, 10, 11, 12, 13, 14 or more amino acids. In embodiments, the library comprises cyclic peptides comprising loop lengths of 3, 4, 5, 6, 7, 8, 9, 10, 11, 12, 13 and 14 amino acids. In embodiments, the library comprises cyclic peptides comprising loop lengths of 3, 4, 5, 6, 7, 8, 9, 10, 11, 12, 13, 14, 15 or more amino acids. In embodiments, the library comprises cyclic peptides comprising loop lengths of 3, 4, 5, 6, 7, 8, 9, 10, 11, 12, 13, 14 and 15 amino acids. In embodiments, the library comprises cyclic peptides comprising loop lengths of 3, 4, 5, 6, 7, 8, 9, 10, 11, 12, 13, 14, 15, 16 or more amino acids. In embodiments, the library comprises cyclic peptides comprising loop lengths of 3, 4, 5, 6, 7, 8, 9, 10, 11, 12, 13, 14, 15 and 16 amino acids.

In an aspect, the library comprises cyclic peptides having two or more loops. In embodiments, the library comprises peptides comprising 0, 1, 2, 3, 4, 5, 6 or 7 or more loops. In embodiments, the library comprises peptides comprising 0, 1, 2, 3, 4, 5, 6 and 7 loops. In embodiments, the library comprises peptides comprising 0, 1, 2, or more loops. In embodiments, the library comprises peptides comprising 0, 1, and 2 loops. In embodiments, the library comprises peptides comprising 0, 1, 2, 3 or more loops. In embodiments, the library comprises peptides comprising 0, 1, 2 and 3 loops. In embodiments, the library comprises peptides comprising 0, 1, 2, 3, 4 or more loops. In embodiments, the library comprises peptides comprising 0, 1, 2, 3 and 4 loops. In embodiments, the library comprises peptides comprising 0, 1, 2, 3, 4, 5 or more loops. In embodiments, the library comprises peptides comprising 0, 1, 2, 3, 4 and 5 loops. In embodiments, the library comprises peptides comprising 0, 1, 2, 3, 4, 5, 6 or more loops. In embodiments, the library comprises peptides comprising 0, 1, 2, 3, 4, 5 and 6 loops.

The present disclosure provides such a design as specific positions are selected to encode either a cysteine residue or another amino acid, wherein the ratio selected enables a higher proportion of cyclic peptides as compared to linear peptides to be displayed and expressed as compared to randomized linear peptide libraries.

A linear peptide library of 20 codons randomized using NNN or NNK technology has a probability of 12.8% that each member contains two or more cysteine residues.

An embodiment of the present disclosure therefore provides a library comprising linear and constrained, for example, cyclic, peptides, wherein the proportion of members comprising constrained peptides is 13% or more, 14% or more, 15% or more, 16% or more, 17% or more, 18% or more, 19% or more, 20% or more, 21% or more, 22% or more, 23% or more, 24% or more, or 25% or more.

In another embodiment the present disclosure provides a library comprising linear and cyclic peptides, wherein the proportion of members comprising cyclic peptides is 13% or more, 14% or more, 15% or more, 16% or more, 17% or more, 18% or more, 19% or more, 20% or more, 21% or more, 22% or more, 23% or more, 24% or more, or 25% or more. By controlling the ratio of cysteines at various positions, the present disclosure provides peptide libraries that have a high diversity of conformations useful in many situations, as the library presents both linear, and cyclic peptides, where the cyclic peptides have multiple different lengths of disulfide bond formed loops ranging from, e.g., 3-17 amino acids in length, thus allowing for a large diversity of conformations being presented in the library. In addition, such design produces peptides having 0, 1, 2 or more cysteine residues, allowing for the production of peptides having even more than one or even more than two loops, thus diversifying the conformations presented even more.

In certain embodiments the present disclosure provides a library of synthetic peptides, wherein each member of the library comprises an amino acid sequence Cmix-(X) m-(Amix) n, wherein
  a) Cmix is a mixture of 50% cysteine and an equal mixture of the remaining natural occurring amino acids,
  b) X are each an equal mixture of the natural occurring amino acids, excluding cysteine,
  c) Amix are each a mixture of 5-50% cysteine and an equal mixture of the remaining natural occurring amino acids, and
  d) m and n are both, and independently from each other, 3-20.

In certain embodiments m is 3 and n is 3, 4, 5, 6, 7, 8, 9, 10, 11, 12, 13, 14, 15, 16, 17, 18, 19, or 20. In certain embodiments m is 4 and n is 3, 4, 5, 6, 7, 8, 9, 10, 11, 12, 13, 14, 15, 16, 17, 18, 19, or 20. In certain embodiments m is 5 and n is 3, 4, 5, 6, 7, 8, 9, 10, 11, 12, 13, 14, 15, 16, 17, 18, 19, or 20. In certain embodiments m is 6 and n is 3, 4, 5, 6, 7, 8, 9, 10, 11, 12, 13, 14, 15, 16, 17, 18, 19, or 20. In certain embodiments m is 7 and n is 3, 4, 5, 6, 7, 8, 9, 10, 11, 12, 13, 14, 15, 16, 17, 18, 19, or 20. In certain embodiments m is 8 and n is 3, 4, 5, 6, 7, 8, 9, 10, 11, 12, 13, 14, 15, 16, 17, 18, 19, or 20. In certain embodiments m is 9 and n is 3, 4, 5, 6, 7, 8, 9, 10, 11, 12, 13, 14, 15, 16, 17, 18, 19, or 20. In certain embodiments m is 10 and n is 3, 4, 5, 6, 7, 8, 9, 10, 11, 12, 13, 14, 15, 16, 17, 18, 19, or 20. In certain embodiments m is 11 and n is 3, 4, 5, 6, 7, 8, 9, 10, 11, 12, 13, 14, 15, 16, 17, 18, 19, or 20. In certain embodiments m is 12 and n is 3, 4, 5, 6, 7, 8, 9, 10, 11, 12, 13, 14, 15, 16, 17, 18, 19, or 20. In certain embodiments m is 13 and n is 3, 4, 5, 6, 7, 8, 9, 10, 11, 12, 13, 14, 15, 16, 17, 18, 19, or 20. In certain embodiments m is 14 and n is 3, 4, 5, 6, 7, 8, 9, 10, 11, 12, 13, 14, 15, 16, 17, 18, 19, or 20. In certain embodiments m is 15 and n is 3, 4, 5, 6, 7, 8, 9, 10, 11, 12, 13, 14, 15, 16, 17, 18, 19, or 20. In certain embodiments m is 16 and n is 3, 4, 5, 6, 7, 8, 9, 10, 11, 12, 13, 14, 15, 16, 17, 18, 19, or 20. In certain embodiments m is 17 and n is 3, 4, 5, 6, 7, 8, 9, 10, 11, 12, 13, 14, 15, 16, 17, 18, 19, or 20. In certain embodiments m is 18 and n is 3, 4, 5, 6, 7, 8, 9, 10, 11, 12, 13, 14, 15, 16, 17, 18, 19, or 20. In certain embodiments m is 19 and n is 3, 4, 5, 6, 7, 8, 9, 10, 11, 12, 13, 14, 15, 16, 17, 18, 19, or 20. In certain embodiments m is 20 and n is 3, 4, 5, 6, 7, 8, 9, 10, 11, 12, 13, 14, 15, 16, 17, 18, 19, or 20.

In certain embodiments n is 3 and m is 3, 4, 5, 6, 7, 8, 9, 10, 11, 12, 13, 14, 15, 16, 17, 18, 19, or 20. In certain embodiments n is 4 and m is 3, 4, 5, 6, 7, 8, 9, 10, 11, 12, 13, 14, 15, 16, 17, 18, 19, or 20. In certain embodiments n is 5 and m is 3, 4, 5, 6, 7, 8, 9, 10, 11, 12, 13, 14, 15, 16, 17, 18, 19, or 20. In certain embodiments n is 6 and m is 3, 4, 5, 6, 7, 8, 9, 10, 11, 12, 13, 14, 15, 16, 17, 18, 19, or 20. In certain embodiments n is 7 and m is 3, 4, 5, 6, 7, 8, 9, 10, 11, 12, 13, 14, 15, 16, 17, 18, 19, or 20. In certain embodiments n is 8 and m is 3, 4, 5, 6, 7, 8, 9, 10, 11, 12, 13, 14, 15, 16, 17, 18, 19, or 20. In certain embodiments n is 9 and m is 3, 4, 5, 6, 7, 8, 9, 10, 11, 12, 13, 14, 15, 16, 17, 18, 19, or 20. In certain embodiments n is 10 and m is 3, 4, 5, 6, 7, 8, 9, 10, 11, 12, 13, 14, 15, 16, 17, 18, 19, or 20. In certain embodiments n is 11 and m is 3, 4, 5, 6, 7, 8, 9, 10, 11, 12, 13, 14, 15, 16, 17, 18, 19, or 20. In certain embodiments n is 12 and m is 3, 4, 5, 6, 7, 8, 9, 10, 11, 12, 13, 14, 15, 16, 17, 18, 19, or 20.

In certain embodiments n is 13 and m is 3, 4, 5, 6, 7, 8, 9, 10, 11, 12, 13, 14, 15, 16, 17, 18, 19, or 20. In certain embodiments n is 14 and m is 3, 4, 5, 6, 7, 8, 9, 10, 11, 12, 13, 14, 15, 16, 17, 18, 19, or 20. In certain embodiments n is 15 and m is 3, 4, 5, 6, 7, 8, 9, 10, 11, 12, 13, 14, 15, 16, 17, 18, 19, or 20. In certain embodiments n is 16 and m is 3, 4, 5, 6, 7, 8, 9, 10, 11, 12, 13, 14, 15, 16, 17, 18, 19, or 20. In certain embodiments n is 17 and m is 3, 4, 5, 6, 7, 8, 9, 10, 11, 12, 13, 14, 15, 16, 17, 18, 19, or 20. In certain embodiments n is 18 and m is 3, 4, 5, 6, 7, 8, 9, 10, 11, 12, 13, 14, 15, 16, 17, 18, 19, or 20. In certain embodiments n is 19 and m is 3, 4, 5, 6, 7, 8, 9, 10, 11, 12, 13, 14, 15, 16, 17, 18, 19, or 20. In certain embodiments n is 20 and m is 3, 4, 5, 6, 7, 8, 9, 10, 11, 12, 13, 14, 15, 16, 17, 18, 19, or 20.

In certain embodiments, (Amix) comprises 5%, 10%, 15%, 20%, 25%, 30%, 35%, 40%, 45%, or 50% cysteine, and an equal mixture of the remaining natural occurring amino acids.

In certain embodiments the library comprises cyclic peptides having disulfide formed loops of 3, 4, 5, 6, 7, 8, 9, 10, 11, 12, 13, 14, 15, 16, 17, 18, 19, 20 amino acids in length.

In certain embodiments the library comprises synthetic peptides that are 9 or more amino acids in length, 10 or more amino acids in length, 11 or more amino acids in length, 12 or more amino acids in length, 13 or more amino acids in length, 14 or more amino acids in length, 15 or more amino acids in length, 16 or more amino acids in length, 17 or more amino acids in length, 18 or more amino acids in length, 19 or more amino acids in length, 20 or more amino acids in length, 21 or more amino acids in length, 22 or more amino acids in length, 23 or more amino acids in length, 24 or more amino acids in length, 25 or more amino acids in length, 26 or more amino acids in length, 27 or more amino acids in length, 28 or more amino acids in length, 29 or more amino acids in length, 30 or more amino acids in length, 31 or more amino acids in length, 32 or more amino acids in length, 33 or more amino acids in length, 34 or more amino acids in length, 35 or more amino acids in length, 36 or more amino acids in length, 37 or more amino acids in length, 38 or more amino acids in length, 39 or more amino acids in length, 40 or more amino acids in length, 41 or more amino acids in length or 42 or more amino acids in length.

In certain embodiments the present disclosure provides a library of synthetic peptides, wherein each member of the library comprises an amino acid sequence Cmix-(X)m-(Amix) n, wherein
 a) Cmix is a mixture of 50% cysteine and an equal mixture of the remaining natural occurring amino acids,
 b) X are each an equal mixture of the natural occurring amino acids, excluding cysteine,
 c) Amix are each a mixture of 10-20% cysteine and an equal mixture of the remaining natural occurring amino acids,
 d) m is 5 or 6, and
 e) n is 3-20.

In certain embodiments m is 3, 4, 5, 6, 7, 8, 9, 10, 11, 12, 13, 14, 15, 16, 17, 18, 19, or 20.

In certain embodiments n is 3, 4, 5, 6, 7, 8, 9, 10, 11, 12, 13, 14, 15, 16, 17, 18, 19, or 20.

In certain embodiments, (Amix) comprises a mixture of 10-20% cysteine and an equal mixture of the remaining natural occurring amino acids. In a preferred embodiment, (Amix) comprises a mixture of 15% cysteine and an equal mixture of the remaining natural occurring amino acids.

In certain embodiments m is 5 and n is 3, 4, 5, 6, 7, 8, 9, 10, 11, 12, 13, 14, 15, 16, 17, 18, 19, or 20. In certain embodiments m is 6 and n is 3, 4, 5, 6, 7, 8, 9, 10, 11, 12, 13, 14, 15, 16, 17, 18, 19, or 20.

In certain embodiments, the natural occurring amino acids are selected from A, C, D, E, F, G, H, I, K, L, M, N, P, Q, R, S, T, V, W, and Y.

In certain embodiments the present disclosure provides a library of synthetic peptides, wherein each member of the library comprises an amino acid sequence (X) l Cmix-(X)m-(Amix) n, wherein
 a) Cmix is a mixture of 50% cysteine and an equal mixture of the remaining natural occurring amino acids,
 b) X are each an equal mixture of the natural occurring amino acids, excluding cysteine,
 c) Amix are each a mixture of 10-20% cysteine and an equal mixture of the remaining natural occurring amino acids,
 d) m is 5 or 6,
 e) n is 3-20, and
 f) l is 1-3.

In certain embodiments, l is 1, 2 or 3.

In certain embodiments l is 1 and m is 5 and n is 3, 4, 5, 6, 7, 8, 9, 10, 11, 12, 13, 14, 15, 16, 17, 18, 19, or 20. In certain embodiments l is 1 and m is 6 and n is 3, 4, 5, 6, 7, 8, 9, 10, 11, 12, 13, 14, 15, 16, 17, 18, 19, or 20.

In certain embodiments l is 2 and m is 5 and n is 3, 4, 5, 6, 7, 8, 9, 10, 11, 12, 13, 14, 15, 16, 17, 18, 19, or 20. In certain embodiments l is 2 and m is 6 and n is 3, 4, 5, 6, 7, 8, 9, 10, 11, 12, 13, 14, 15, 16, 17, 18, 19, or 20.

In certain embodiments l is 3 and m is 5 and n is 3, 4, 5, 6, 7, 8, 9, 10, 11, 12, 13, 14, 15, 16, 17, 18, 19, or 20. In certain embodiments l is 3 and m is 6 and n is 3, 4, 5, 6, 7, 8, 9, 10, 11, 12, 13, 14, 15, 16, 17, 18, 19, or 20.

An embodiment of the present disclosure provides a peptide library having a design as shown in FIG. 1.

In certain embodiments the present disclosure provides a library of synthetic peptides wherein each member of the library comprises an amino acid sequence (X) l-Cmix-(X)m-(Amix)n, wherein
 a) Cmix is a mixture of 50% cysteine and an equal mixture of the remaining natural occurring amino acids,
 b) X are each an equal mixture of the natural occurring amino acids, excluding cysteine, and
 c) Amix are each a mixture of 15% cysteine and an equal mixture of the remaining natural occurring amino acids
 d) l is 3
 e) m is 6, and
 f) n is 10.

In certain embodiments the peptide library is displayed on bacteriophage. Phage display is known to have significant advantages in allowing the rapid selection of useful molecules. This method allows the preparation of libraries as large as $10^{10}$ unique peptide members, many orders of magnitude larger than libraries that may be prepared synthetically. Using such a robust platform allows for the display of large, diverse libraries.

In one embodiment, the library of the instant invention contains at least about $10^7$ member peptides, each of which has at least one amino acid variation from others. Alternatively, the library contains at least about $10^8$ peptides, or at least about $10^9$ peptides.

In certain embodiments the library comprises constrained and/or cyclic peptides which are formed by disulfide bonds between two or more cysteines, zinc-finger domains, a jun-fos interaction, a leucine zipper, thioether bonds, such as the thioether bonds which are formed and/or which are present in lanthionines, or lysinoalanine linkages.

In certain embodiments, the peptide library comprises constrained, for example, cyclic, peptides which are formed by disulfide bonds between two or more cysteine residues. In certain embodiments, the peptide library comprises cyclic peptides which are formed by disulfide bonds between two or more cysteine residues.

In certain embodiments, the library comprises cyclic or constrained peptides which are formed by disulfide bonds between two or more cysteine residues, wherein the two or more cysteine residues are not located at the N or the C-terminus of the peptide, or are located at either the N or the C-terminus of the peptide, but seldom both.

In certain embodiments the present invention provides peptide libraries comprising peptides greater than 16 amino acids in length. In other embodiments the present invention provides libraries comprising peptides having 20 amino acids in length.

In certain embodiments the present invention provides peptide libraries wherein a portion of the peptides comprise 0, 1, or 2 or more cysteine residues.

In certain embodiments the present invention provides a library of nucleic acids encoding the libraries of peptides of the present disclosure.

In certain embodiments the present invention provides a vector comprising the nucleic acids encoding the libraries of peptides of the present disclosure.

In certain embodiments, the vector is a display vector. In other embodiments, the vector is an expression vector.

In certain embodiments the present disclosure provides a method of identifying a peptide specific for an antigen, comprising
  a) contacting an antigen with a library of peptides disclosed herein, and
  b) selecting one or more peptides specific for said antigen.

In certain embodiments the present disclosure provides a peptide identified using the library of peptides disclosed herein.

Phage Display Methods

Phage display methods for proteins, peptides and mutated variants thereof, including constructing a family of variant replicable vectors containing a transcription regulatory element operably linked to a gene fusion encoding a fusion polypeptide. transforming suitable host cells, culturing the transformed cells to form phage particles which display the fusion polypeptide on the surface of the phage particle, contacting the recombinant phage particles with a target molecule so that at least a portion of the particle bind to the target, separating the particles which bind from those that do not bind, are known and may be used with the libraries disclosed herein.

In certain embodiments the peptides are fused to at least a portion of a phage coat protein to form a fusion protein containing the peptide disclosed herein. The fusion protein can be made by expressing a gene fusion encoding the fusion protein using known techniques of phage display. The fusion protein may form part of a phage or phagemid particle in which one or more copies of the peptide are displayed on the surface of the particle. An embodiment includes a nucleic acid encoding the peptide or the fusion proteins described herein.

In certain embodiments the present disclosure provides vectors comprising the fusion genes noted above, as well as a library of these vectors. The library of vectors may be in the form of a DNA library, a library of virus (phage or phagemid) particles containing the library of fusion genes or in the form of a library of host cells containing a library of the expression vectors or virus particles.

In certain embodiments the present disclosure provides a method comprising the steps of preparing a library containing a plurality of vectors, each vector comprising a transcription regulatory element operably linked to a gene fusion encoding a fusion protein, wherein the gene fusion comprises a first gene encoding a peptide disclosed herein and a second gene encoding at least a portion of a phage coat protein, wherein the library comprises a plurality of genes encoding peptide fusion proteins.

The gene encoding the coat protein of the phage and the gene encoding the desired polypeptide portion of the fusion protein of the invention (the peptide of the invention fused to at least a portion of a phage coat protein) can be obtained by methods known in the art (see generally, Sambrook et al) The DNA encoding the gene may be chemically synthesized (Merrfield (1963) 7 Am Chem Soc 85:2149).

The phage coat protein is preferably the gene III or gene VIII coat protein of a filamentous phage, such as, M13.

Suitable gene III vectors for display of peptides include fUSE5 (Scott. J K. and Smith G P (1990) Science 249 386-390), fAFFI (Cwirla et al (1990) Proc Natl Acad Set USA 87 6378-6382), fd-CATI (McCafferty et al (1990) Nature (London) 348 552-554), m663 (Fowlkes et al (1992) Biotechniques 13 422-427), tdtetDOG. pHEN I (Hoogenboom et al (1991) Nucleic Acids Res 19 4133-4137) pComb3 (Gram et al (1992) Proc Natl Acad Sc i USA 89 3576-3580), pCANTAB 5E (Pharmacia), and LamdaSurt ap (Hogrefe (1993) Gene 137 85-91) Suitable phage and phagemid vectors for use in this invention include all known vectors for phage display Additional examples include pCombo (Gram et al. (1992) Proc. Natl. Acad. Sci. USA 89:3576-3580), pC89 (Fehci et al. (1991) 7. Mol. Biol. 222:310-310); plF4 (Bianchi et al. (1995) 7. Mol. Biol. 247: 154-160); PM48. PM52. and PM54 (Iannolo. (1995) 7. Mol. Biol 248:835-844); fdH (Greenwood et al. (1991) 7. Mol. Biol. 220:821-827); pfdoSHU, pfd8SU, pfd8SY, and fdISPLAY8 (Malik & Perham (1996) Gene 171:49-51); "88" (Smith (1993) Gene 128: 1-2); f88.4 (Zhong et al. (1994) 7. Biol. Chem, 269:24183-24188); p8V5 (Affymax); MB 1, MB20, MB26, MB27. MB28, MB42. MB48. MB49. MB56: (Markland et al. (1991) Gene 109: 13-19). Similarly, any known helper phage may be used when a phagemid vector is employed in the phage display system. Examples of suitable helper phage include M 13-K07 (Pharmacia), M 13-VCS (Stratagene), and R408 (Stratagene).

Any suitable cells which can be transformed by electroporation may be used as host cells in the method of the present invention. Suitable host cells which can be transformed include gram negative bacterial cells such as E. coli. Suitable E. coli strains include TG1 F+, TG1F-, JM 101, E. coli K 12 strain 294 (ATCC number 3 1.446), E. coli strain W31 10 (ATCC number 27.325), E. coli X1776 (ATCC number 31,537), E. coli XL-I Blue (Stratagene). and E. coli B; however many other strains of E. coli, such as XL I-Blue MRF', SURE. ABLE C. ABLE K. WM 1 100, MC 1061, HB 101, CJ 136. MV 1 190. JS4, JS5, NM522. NM538, and NM539 may be used as well. Cells are made competent using known procedures. Sambrook et al, 1.76-1.81, 16.30.

In certain embodiments the host cell for electroporation is a competent E. coli strain containing a phage F' episome. Any F' episome which enables phage replication in the strain may be used in the invention.

After selection of the transformed cells, these cells are grown in culture and the vector DNA may then be isolated. Phage or phagemid vector DNA can be isolated using methods known in the art, for example, as described in Sambrook et al. The isolated DNA can be purified by methods known in the art such as that described in section 140 of Sambrook et al. This purified DNA can then be analyzed by DNA sequencing DNA sequencing may be performed by the method of Messing et al (1981) Nucleic Acids Res 9 309. The method of Maxam et al (1980) Meth Enzymol 65 499, or by any other known method.

Method of Generating Diversified Libraries

Methods of generating diversified gene libraries, such as the Slonomics technology, are disclosed in U.S. Ser. No. 12/414,174, which is incorporated by reference in its entirety, and J. Van den Brulle, M. Fischer, T. Langmann, G. Horn, T. Waldmann, S. Arnold, M. Fuhrmann, O. Schatz, T. O'Connell, D. O'Connell et al. (2008), A novel solid phase technology for high-throughput gene synthesis, Biotechniques, 45, pp. 340-343, which is incorporated by reference in its entirety.

The Slonomics method uses a defined number of standardized building blocks is chemically synthesized as single-stranded oligonucleotides containing self-complementary regions. Intra-strand base pairing of these regions leads to the formation of a stable hairpin-like secondary structure comprising a short loop of four nucleotides, a double-stranded stem region assuring the stability of the molecule, and a three-nucleotide single-stranded overhang.

Two different classes of building blocks are defined as "splinkers" and "anchors." All splinker molecules share the same scaffold structure and differ only in their variable three-base single-stranded overhangs. In contrast, the anchor oligonucleotides differ in the overhang and also in the directly adjacent base triplet.

Figure 13:
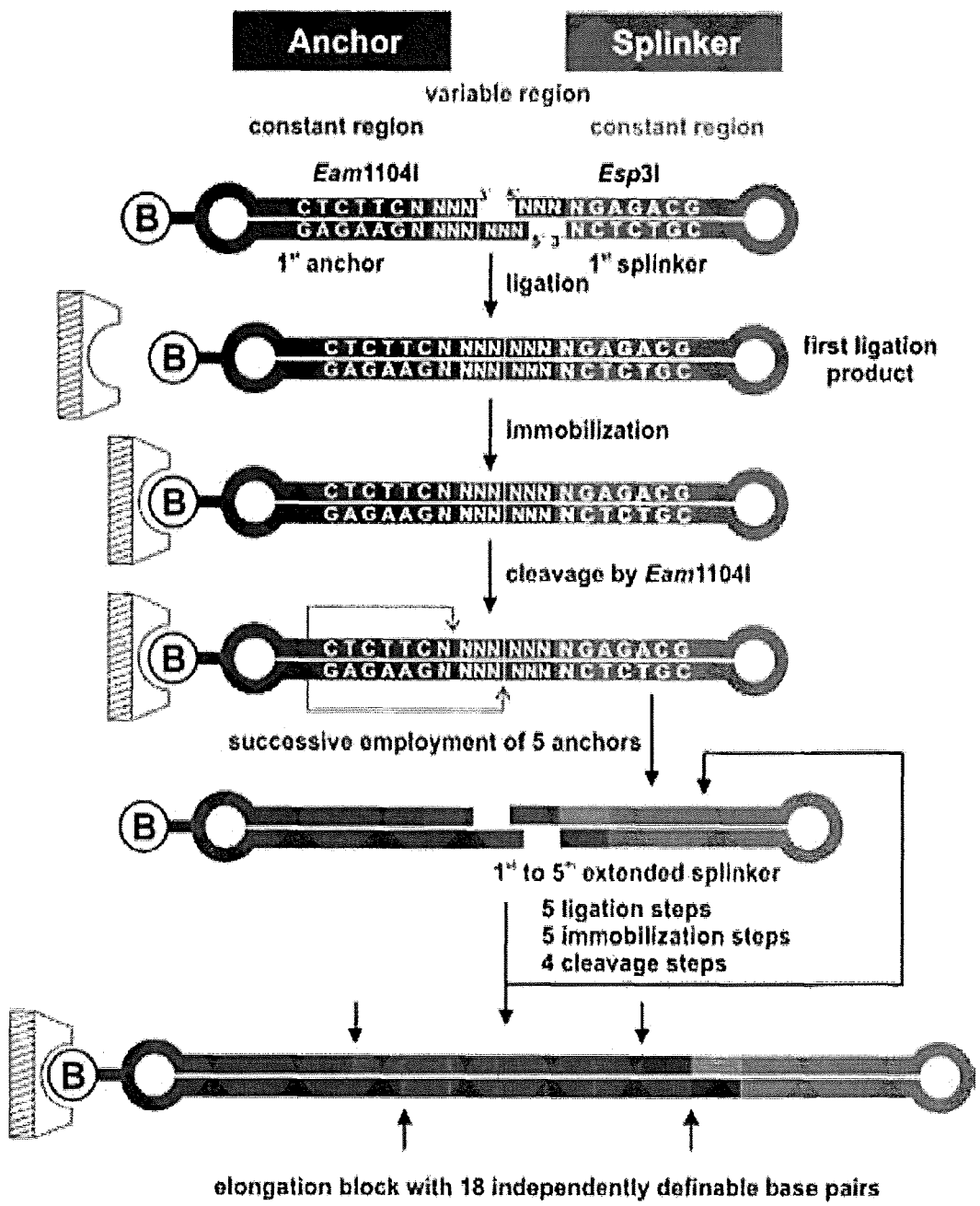
FIG. 13 shows a pictorial representation of a portion of the Slonomics method.

A portion of the Slonomics method is shown in FIG. 13.

In order of their appearance, the above sequences are SEQ ID NO:s 1-5.

In order to create a library representing all possible permutations, 64 ($4^3$) different splinkers and 4096 ($4^6$) different anchor oligonucleotides are required. Each anchor molecule harbors an additional biotin modification in the loop region, allowing the oligonucleotide to be coupled to a streptavidin-coated surface with high affinity. The two types of oligonucleotides are further characterized by the presence of different recognition sites for type IIS restriction enzymes within their stem regions. The anchor oligonucleotide contains a recognition site for Earn 11041 (CTCTTC[1/4], generating a three-base overhang) and the corresponding splinker molecule harbors a recognition site for Esp3I (CGTCTC[1/5], generating a four-base overhang).

To construct a large double-stranded DNA fragment from these molecular building blocks, the sequence is first assembled as smaller sub-fragments of 18 bp. These so-called "elongation blocks" can be synthesized in parallel reactions. In the first step, one anchor and one splinker molecule are ligated via hybridization (Watson-Crick base pairing) of complementary single-stranded overhangs. Generally, this step is performed in solution, since enzymatic reactions in solution occur at much faster rates than those on solid supports, where diffusion pathways are much longer. Following ligation, the resulting product is immobilized on a streptavidin-coated 96-well plate via the biotin modification of the anchor molecule. Non-reacted material is removed in a washing step. The remaining surface-bound ligation products are subsequently cleaved by Eam1104I, which is specific for the anchor that donates the base triplet block. The cleavage of the ligation product by this restriction enzyme releases an elongated, highly pure "intermediate product" that has a new three-base single-stranded overhang and serves as an acceptor for the next anchor molecule. Thus, this reaction cycle results in the incorporation of three new bases to the growing chain and a shortened anchor that remains bound to the surface. This reaction cycle is repeated five times to produce an 18 bp DNA fragment. For optimal reaction performance, the anchor molecules and the intermediate products should be present in equimolar concentrations. If one of the ligation partners is in excess, resulting in a mixture of correct, immobilized higher level ligation products and unreacted precursors, unligated intermediate products can be removed efficiently by washing, while unligated anchors remain bound to the surface after cleavage.

The complete synthesis process comprises two distinct phases. During the initial "elongation" phase, short sub-sequences of the target molecule are produced as described above, resulting in individual elongation blocks with 18 independently definable base pairs. Since many of these reactions can be performed in parallel, the entire target sequence is already constructed during the initial elongation process, albeit as a series of short sub-fragments. In the second reaction phase, the so called "transposition," the pre-assembled elongation blocks are connected in a pair-wise fashion after each block has been cleaved with the appropriate type IIS restriction enzyme. Restriction with Eam1104I results in the release of the elongation block from the surface and thereby generates a three-base overhang. Cleavage with Esp3l removes the splinker-component of the molecule, leading to a four-base overhang. The resulting molecules can be assembled in a highly selective manner due to the different length and specific sequences of their overhangs.

Figure 14:
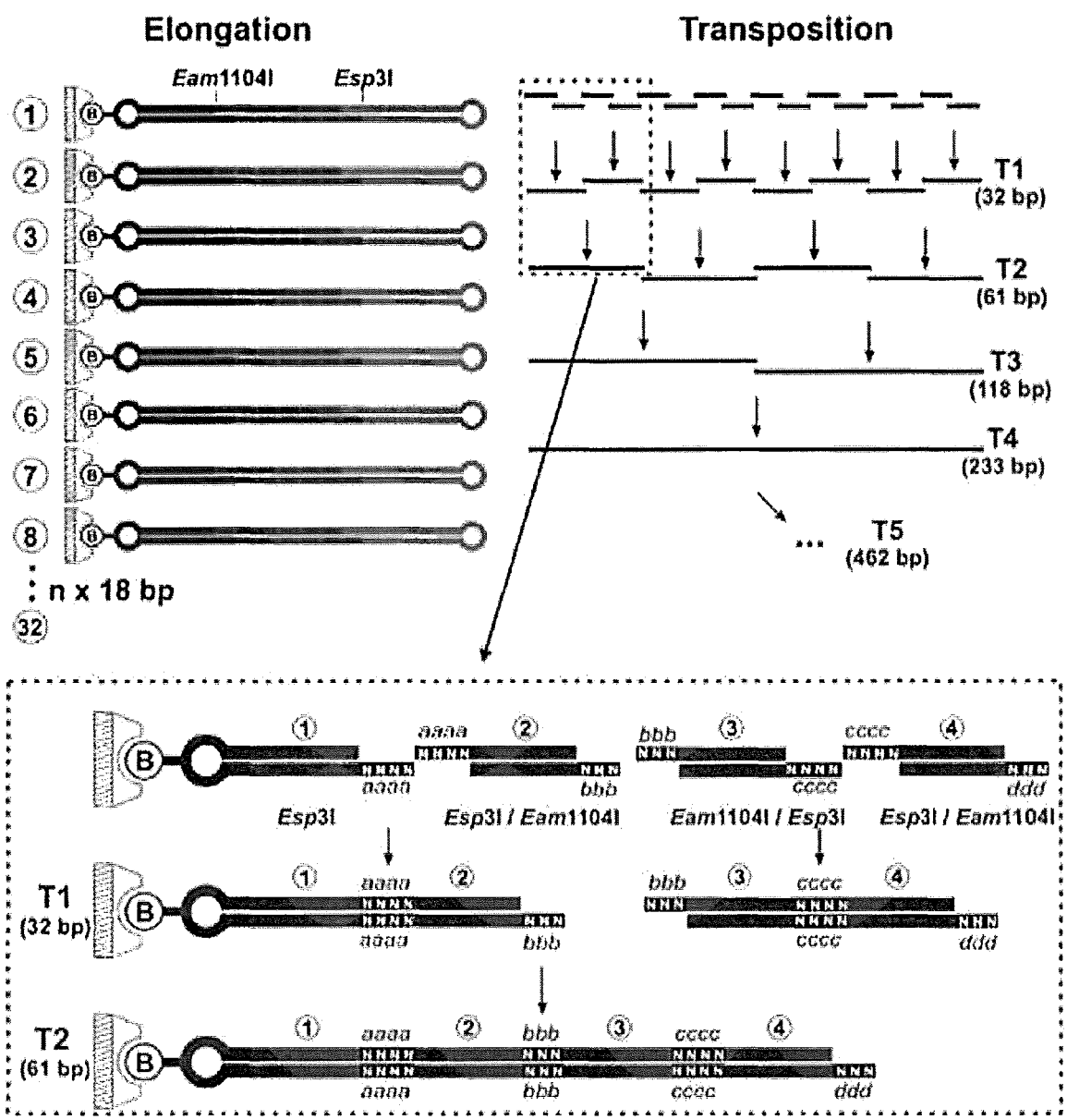
FIG. 14 shows a pictorial representation of a portion of the Slonomics method.

A further portion of the Slonomics method is shown in FIG. 14.

Additionally, depending on the restriction by Eam1104I, the ligation reactions can be performed at the solid surface or in solution, which allows for the focus to be on either product purity or yield. Since the resulting molecules still harbor the constant anchor and splinker regions at their terminal ends, this reaction cycle (including washing steps) can be repeated several times, each round resulting in DNA molecules that have doubled in length with respect to those of the previous round. At different transposition stages, the resulting constructs are "harvested" from the solid surface by cleavage and transferred from the automated production platform to a second standardized system for the final assembly and quality control. Each transposition can be developed robustly up to the T5 level (5 transposition rounds), corresponding to a fragment length of 462 bp. If necessary, these "T5-building blocks" can be further assembled by standard recombinant DNA technology.

The Slonomics® technology is also highly efficient and cost-effective. In contrast to classical strategies, where each oligonucleotide is individually designed and used for a single synthesis reaction, our building blocks are used for multiple reactions over the course of several synthesis projects. In addition, all steps of the process can be done in parallel, which allows for the simultaneous production of several gene constructs and enables the transfer of every working step to a robotic platform. The complete synthesis is performed in multi-well plates, and hardware components with demonstrated suitability for robust production processes have been combined in an entirely computer-controlled system. This permits the fully-automated synthesis of any 462 bp DNA fragment, from design to end product, within a time frame of 44 hours.

Oligonucleotide-mediated mutagenesis is another method for preparing diversified gene libraries. This technique is well known in the art as described by Zoller et al (1987) Nucleic Acids. Res. 10 6487-6504.

Cassette mutagenesis is also a method for preparing the diversified gene libraries. The method is based on that described by Wells et al. (1985) Gene 34:315.

The following examples are provided by way of illustration and not by way of limitation. All disclosures of the references cited herein are expressly incorporated herein by reference in their entirety.

Embodiments

An aspect comprises a library of synthetic peptides comprising linear and cyclic peptides, wherein the proportion of cyclic peptides within said library is greater than 13%.

In an aspect, a library of peptides comprises (a) linear and cyclic peptides, (b) cyclic peptides having different loop lengths, and (c) cyclic peptides having two or more loops.

In an aspect, a library of peptides, comprises linear and cyclic peptides, wherein the cyclic peptides have different loop lengths, and wherein the cyclic peptides have two or more loops.

In embodiments, the library comprises synthetic peptides.

In embodiments, the library comprises peptides translated from nucleic acids.

In embodiments, the library comprises peptides having a controlled ratio of cysteines at certain positions.

In an aspect, a library of peptides consists of (a) linear and cyclic peptides, (b) cyclic peptides having different loop lengths, and (c) cyclic peptides having two or more loops.

In embodiments, the library comprises cyclic peptides with loop lengths ranging from 3-17 amino acids in length. In embodiments, the library comprises cyclic peptides comprising loop lengths of 3, 4, 5, 6, 7, 8, 9, 10, 11, 12, 13, 14, 15, 16, or 17 amino acids. In embodiments, the library comprises cyclic peptides comprising loop lengths of 3, 4, 5, 6, 7, 8, 9, 10, 11, 12, 13, 14, 15, 16, and 17 amino acids.

In embodiments, the library consists of cyclic peptides with loop lengths ranging from 3-17 amino acids in length. In embodiments, the library consists of cyclic peptides comprising loop lengths of 3, 4, 5, 6, 7, 8, 9, 10, 11, 12, 13, 14, 15, 16, or 17 amino acids. In embodiments, the library consists of cyclic peptides comprising loop lengths of 3, 4, 5, 6, 7, 8, 9, 10, 11, 12, 13, 14, 15, 16, and 17 amino acids.

In an aspect, the library comprises cyclic peptides having two or more loops. In embodiments, the library comprises peptides comprising 0, 1, 2, 3, 4, 5, 6 or 7 or more loops. In embodiments, the library comprises peptides comprising 0, 1, 2, 3, 4, 5, 6 and 7 loops.

In an aspect, the library consists of cyclic peptides having two or more loops. In embodiments, the library consists of peptides comprising 0, 1, 2, 3, 4, 5, 6 or 7 or more loops. In embodiments, the library consists of peptides comprising 0, 1, 2, 3, 4, 5, 6 and 7 loops.

In embodiments, the synthetic peptides of the library are displayed on bacteriophage. In embodiments, the synthetic peptides of the library are displayed on ribosomes.

In embodiments, the library comprises at least $1 \times 10^7$ members. In embodiments, the library consists of at least $1 \times 10^7$ members.

In embodiments of the library, the cyclic peptides are formed by one or more covalent or one or more non-covalent bonds.

In embodiments of the library, the covalent bond is a disulfide bond or a bond between two non-naturally occurring amino acids, such as, a thioether bond.

In embodiments of the library, the thioether bond is a lanthiopeptide, such as a lanthiopeptide formed between a dehydrated serine and a cysteine or a dehydrated threonine and a cysteine.

In embodiments of the library, the covalent bond is a lysinoalanine linkage formed between a dehydrated serine and a lysine.

In embodiments of the library, the non-covalent bond is a formed via a protein domain, such as, a zinc-finger domain, a jun-fos interaction or a leucine zipper.

In certain embodiments, the covalent bond is a disulfide bond. In certain embodiments, the disulfide bond is formed by two cysteine residues. In certain embodiments, the library comprises peptides comprising 0, 1, 2, 3, 4, 5, 6 or 7 or more cysteine residues. In certain embodiments, the library comprises peptides comprising 0, 1, 2, 3, 4, 5, 6 and 7 cysteine residues.

In certain embodiments, the library consists of peptides comprising 0, 1, 2, 3, 4, 5, 6 or 7 or more cysteine residues. In certain embodiments, the library consists of peptides comprising 0, 1, 2, 3, 4, 5, 6 and 7 cysteine residues.

In embodiments of the library, the synthetic peptides are 9 or more amino acids in length.

In embodiments of the library, each member of the library comprises an amino acid sequence Cmix-(X) m-(Amix) n, wherein
a) Cmix is a mixture of 50% cysteine and an equal mixture of the remaining natural occurring amino acids,
b) X are each an equal mixture of the natural occurring amino acids, excluding cysteine,
c) Amix are each a mixture of 5-50% cysteine and an equal mixture of the remaining natural occurring amino acids, and
d) m and n are both, and independently from each other, 3-20.

In embodiments of the library, each member of the library comprises an amino acid sequence Cmix-(X) m-(Amix) n, wherein
a) Amix are each a mixture of 10-20% cysteine and an equal mixture of the remaining natural occurring amino acids,
b) m is 5-6, and
c) n is 3-20.

In embodiments of the library, each member of the library comprises an amino acid sequence (X) l-Cmix-(X) m-(Amix) n, wherein
a) l is 1-3.

In embodiments of the library, each member of the library comprises an amino acid sequence (X) l-Cmix-(X) m-(Amix) n, wherein
a) Amix are each a mixture of 15% cysteine and an equal mixture of the remaining natural occurring amino acids,
b) l is 3,
c) m is 6, and
d) n is 10.

In embodiments of the library, the library has a design as shown in FIG. 1.

In embodiments of the library, Amix comprises 15% cysteine, and an equal mixture of the remaining natural occurring amino acids.

An aspect includes a library of nucleic acids encoding the libraries disclosed herein.

An aspect includes vector comprising the nucleic acids disclosed herein.

In embodiments the vector is a display vector or an expression vector.

An aspect includes a method of identifying a peptide specific for an antigen, comprising
(a) contacting an antigen with a library as disclosed herein, and
(b) selecting one or more peptides specific for said antigen.

An aspect includes peptide identified using the method described herein.

EXAMPLES

Example 1: Selection of the Appropriate Vectors

First we had to decide on the display vector into which the DNA-library encoding the peptides of the present disclosure will be cloned. Optimal display modes/rates were taken into consideration in the choice of the display vector (gIII- or gVIII-fusion), as well as the optional use of structured or unstructured linkers and additional affinity tags for detection and immobilization. For cloning of the variable library fragment into alternative display vectors suitable restriction enzyme sites were identified for the generation of a fusion with the selected phage proteins.

The use of a phagemid vector, containing a N-terminal fusion of the peptide library sequence to the gene of the minor coat protein pIII, in combination with Hyperphages harboring a pIII gene deletion results in a pentavalent display of the peptides. The pIII protein is present in 5 copies at the distal end of the phage particles and its function is required for phage infectivity by binding to the F-pilus of bacterial cells. Although it is thought that if the displayed peptides are sufficiently short enough (<50 residues) the function of the pIII-fusion would not to be negatively affected and all five copies of the pIII protein can carry displayed peptides, functional impairment of the pIII-peptide fusion cannot be completely excluded. In general, reduced functionality of pIII-fusion proteins, which might result in reduced phage infectivity, can be compensated by the use of Helperphage with a wild-type pIII gene. pVIII is a major capsid protein, therefore, if multivalent display of the peptide library is desired then fusion of the variable peptide to pVIII should be used.

Figure 7:
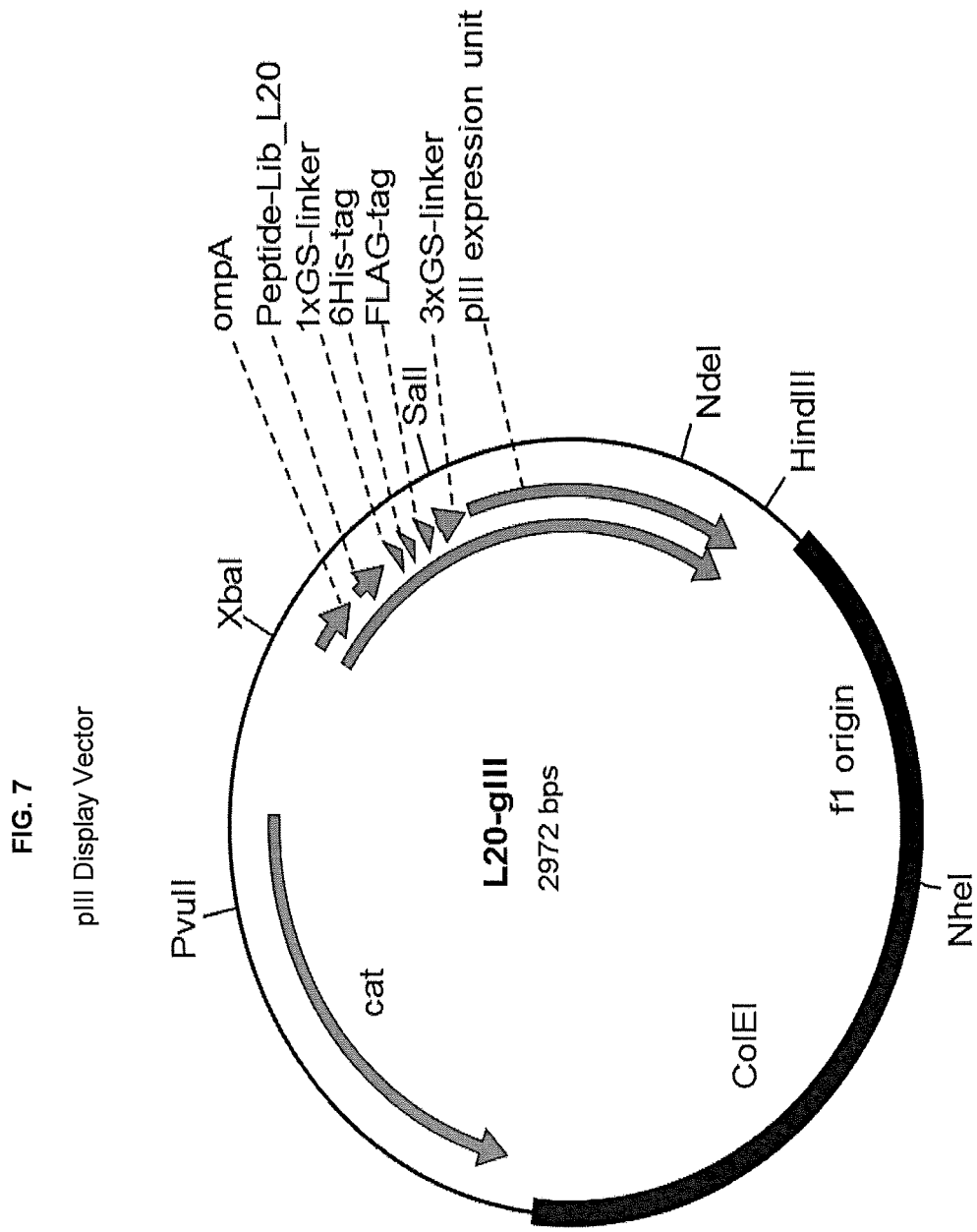
FIG. 7 shows a pIII display vector for use in displaying the peptide libraries disclosed herein.
Figure 8:
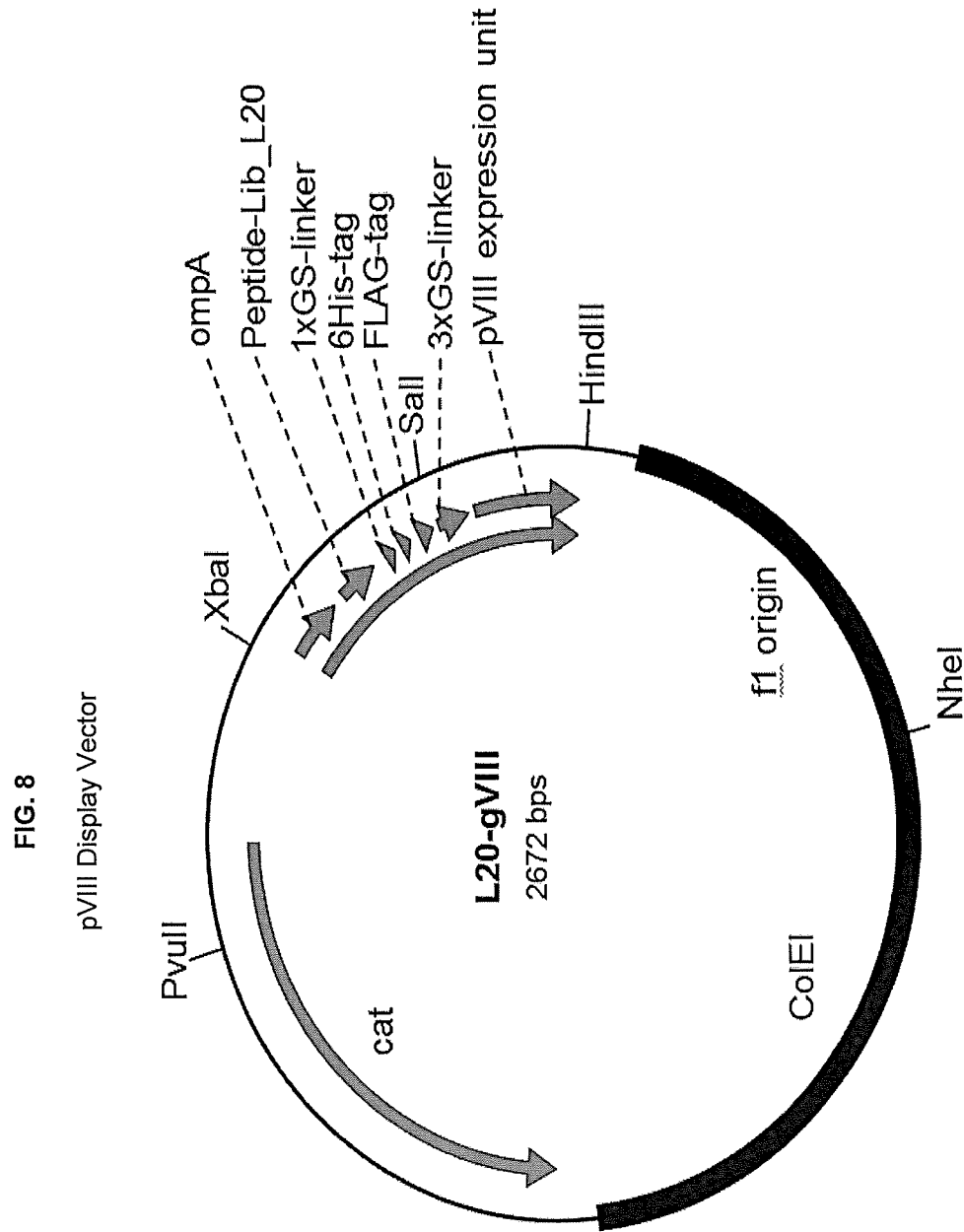
FIG. 8 shows a pVIII display vector for use in displaying the peptide libraries disclosed herein.
Figure 9:
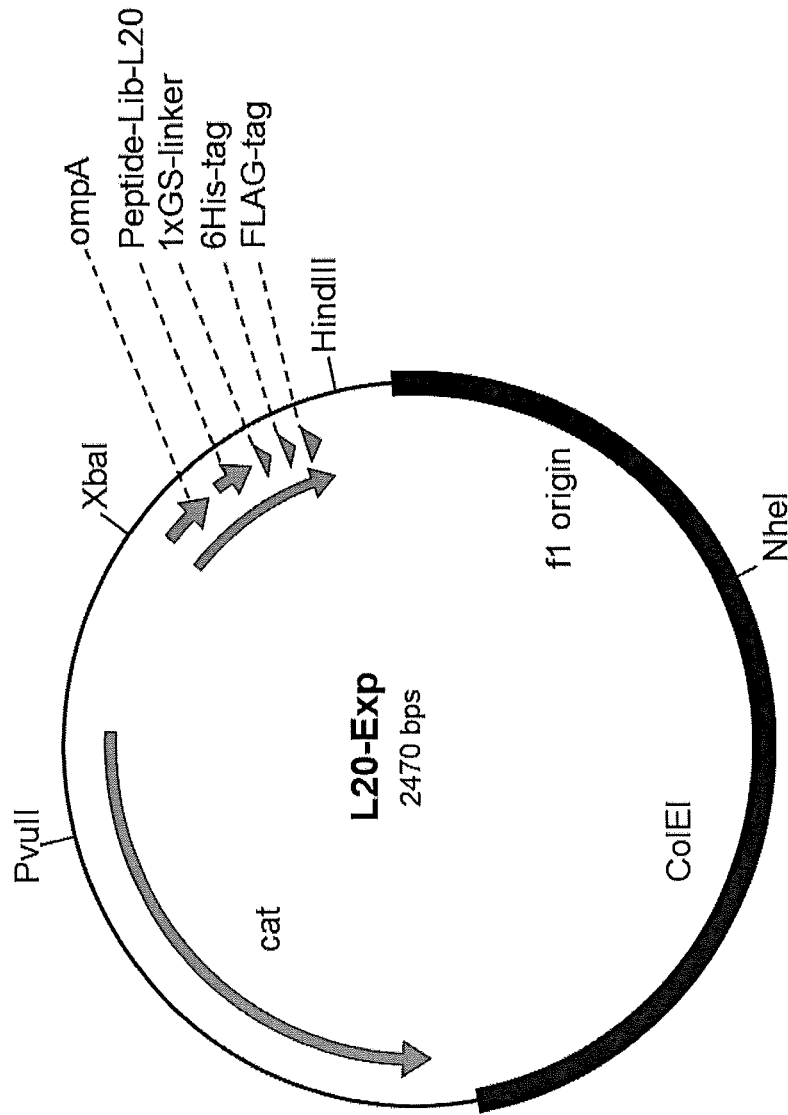
FIG. 9 shows an expression vector for use in expressing the peptides disclosed herein.
Figure 10:
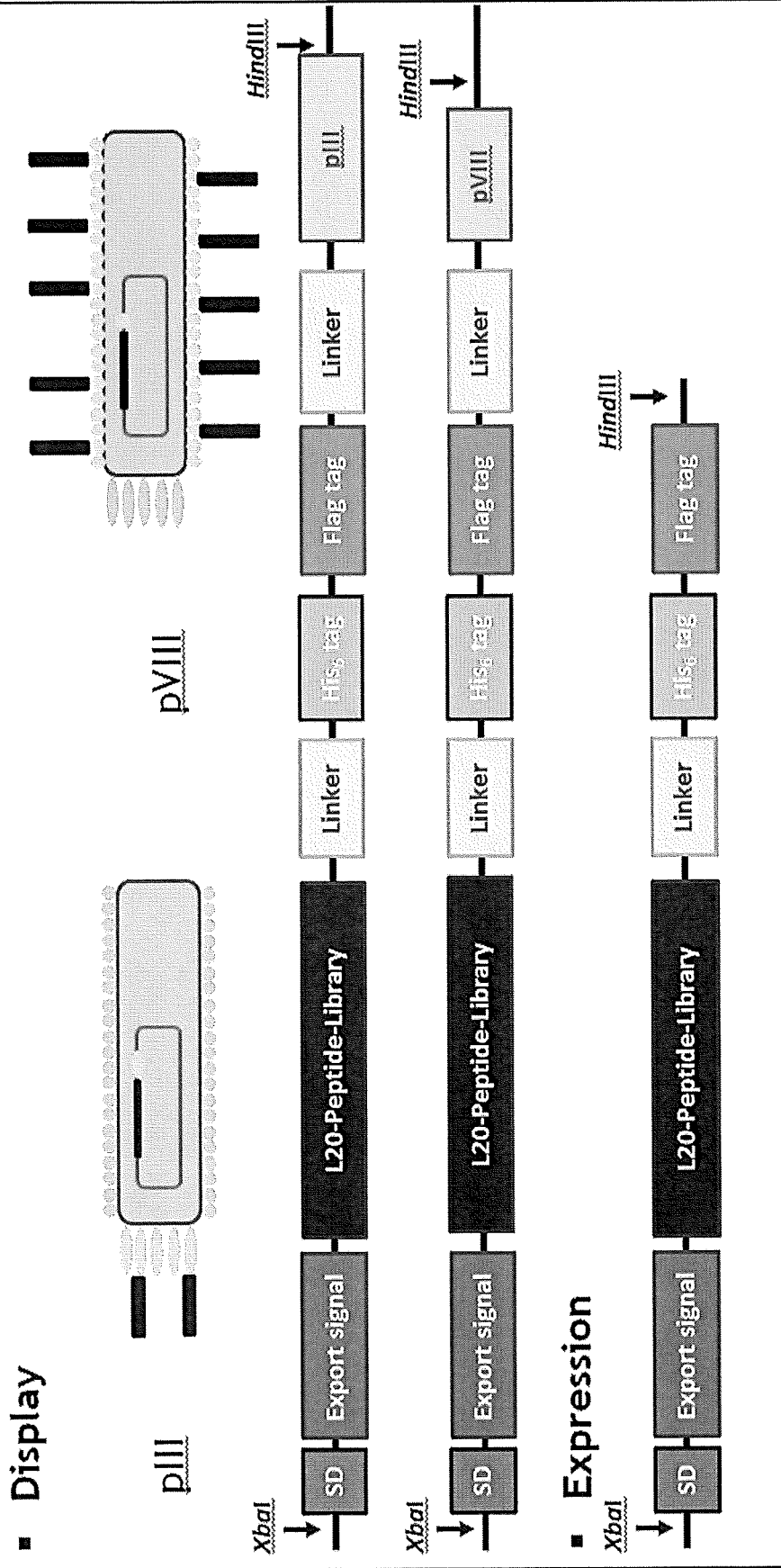
FIG. 10 shows a simplified view of the display and expression vectors for use in displaying the libraries disclosed herein.

Exemplary display vectors for displaying the libraries disclosed herein are shown in FIGS. 7-8 and 10. Exemplary expression vectors for expressing the peptides disclosed herein are shown in FIG. 9.

Example 2: Design of the Peptide Library

In addition to the use of linear peptides, it is advantageous to present cyclic and constrained peptides to facilitate the identification of specific interaction partners in Phage Display experiments. This can be realized by two cysteine residues flanking the variable region resulting in the generation of disulfide bond stabilized circular peptides of fixed size. The Slonomics Technology allows the controlled introduction of such cysteine residues at various desired positions within the variable peptides. The percentage of the cysteine residues at the chosen variable positions can be designed to result in the generation of an average of one to two or more cysteine residues per molecule. Therefore, encoded peptides without cysteine residue or containing only one cysteine residue will be linear, while the encoded peptides with two cysteine residues or more at desired positions will generate cysteine bridged circles of various lengths. Thus with this design, for example the design of FIG. 1, it is possible to generate a universal peptide library containing a defined mixture of linear and circular peptides, thereby offering the possibility of a simultaneous presentation of both alternatives in the same screening experiment. Evidence of a library comprising peptides have a controlled frequency of cysteines at certain positions is shown in FIGS. 2A-C, and 11 and 12.

Example 3: Library Generation

A library having the design shown in FIG. 1 was chosen for display and testing. The DNA fragments containing the peptide library sequence were synthesized as follows: The flanking constant regions comprising a signal sequence, epitope tag and spacer regions were synthesized by gene synthesis. The peptide library encoding sequence with a randomized stretch of 20 amino acids was synthesized by Slonomics. The resulting 333 bp completely synthetic linear DNA fragment comprising the peptide library and flanking constant regions was cloned via XbaI and SalI into the pIII and pVIII display vectors, respectively (FIG. 7 and FIG. 8).

Typically 0.25 to 2 µg of the ligated phagemid DNA of the libraries were used to transform *E. coli* MC1061 F' electrocompetent cells and transformants were collected in TB medium and shaken for at 37° C. for 1 h. Dilutions of the outgrowth medium were plated on LB/Chloramphenicol/Glucose. Amplification of the libraries was performed by shaking o/n in appropriate amounts of LB/Chloramphenicol/1% Glucose. Library sizes for the cloned peptide library-L20-pIII- and -pVIII-fusions ranged between 1.2 E+09 and 4.4E+09.

To analyze the quality of the engineered sub-libraries at least 90 clones for each library were picked and the XbaI/HindIII region was sequenced to determine correctness and uniqueness of the sequences. The libraries were stored as *E. coli* glycerol cultures.

Phage displaying the pIII- and the pVIII-fusions of the L20-peptide library were prepared as follows. For each library phage preparation 80 ml 2×YT/Chloramphenicol/Glucose medium were inoculated with bacteria from the corresponding library glycerol stock resulting in an OD600 nm of 0.2-0.3. Cultures were shaken until an OD600 nm of 0.45-0.55 was reached. Then helper phage was added at a multiplicity of infection of 10 to the bacterial culture followed by an incubation for 45 min at 37° C. without shaking and then for 45 min at 37° C. shaking at 120 rpm. Bacteria were spun down and helper phage containing supernatant was discarded. Phage-infected bacteria were resuspended in 400 ml 2×YT/Chloramphenicol/Kanamycin/IPTG medium and incubated overnight at 22° C. with shaking at 120 rpm. The next day bacteria from the overnight culture were pelleted by centrifugation and the supernatant containing the peptide-presenting phage was collected. Phage precipitation was performed by adding PEG/NaCl to the phage-containing supernatant. The sample was incubated for at least 30 min on ice. Precipitated phage were spun down and resuspended in PBS. The sample was rotated slowly to obtain a homogeneous suspension and residual bacterial debris was pelleted and discarded.

From the phage-containing supernatant the phage were precipitated again using PEG/NaCl. Finally, the phage pellet was resuspended in PBS, transferred to a sterile tube and incubated with gentle agitation to obtain a homogeneous suspension. Phage titers were determined by spot titration and UV absorbance (Nanodrop) at OD268 nm, and ELISA. Display of peptide on the produced phage was evaluated by ELISA. The anti-M13 antibody (Santa Cruz) was used for capturing, as it captures phage particles via the major coat protein g8p. For detection three different antibodies were used. A monoclonal anti-M13 (directed against the major coat protein of M13 phage, g8p) conjugated to HRP (Amersham), and a monoclonal antibody against the FLAG epitope conjugated to AP (AP27, Sigma) or monoclonal anti Histidine antibody conjugated to HRP (R&D Systems), as both epitope tags are encoded by the pIII- and pVIII-peptide libraries and therefore part of the displayed peptides (FIG. 10). The capture antibody was immobilized by dispensing antibody solution for the anti-M13 antibody into the wells of a 96-well Maxisorp plate, sealing the plate with laminated foil and incubating overnight. The next day, the plates were washed 3 times with PBST, and each well was blocked with blocking buffer for at least 1 h at room temperature. After blocking and washing of the plates, dilutions of phage containing supernatants were added to the wells and incubated for 1 h at room temperature. For detection washed plates were either analyzed using QuantaBlu (Pierce) for HRP conjugated antibodies or Attophos fluorescence substrate (Roche, #11681982001) for the AP-conjugated anti-FLAG antibody.

Example 4: Quality Control

Another important aspect is the evaluation of the quality and functionality of the peptide library. A qualitative assessment of the phage library, with respect to amino acid distribution, frequency and redundancy was carried out using Sanger sequencing and Next Generation Sequencing.

99 clones were analyzed from the library design of FIG. 1 using Sanger sequencing, the results of which are shown in FIG. 2A. FIG. 2A shows the position and distribution of each amino acid, including the cysteines, which form the cyclic peptides disclosed herein. Therefore, this figure shows that the design of FIG. 1 successfully produces a library with the desired positions and proportions of cysteines.

FIGS. 2B and 2C confirm these results further, as Next Generation Sequencing shows that the cysteine distribution within the library highly correlates with the predicted cysteine distribution.

Figure 3B:
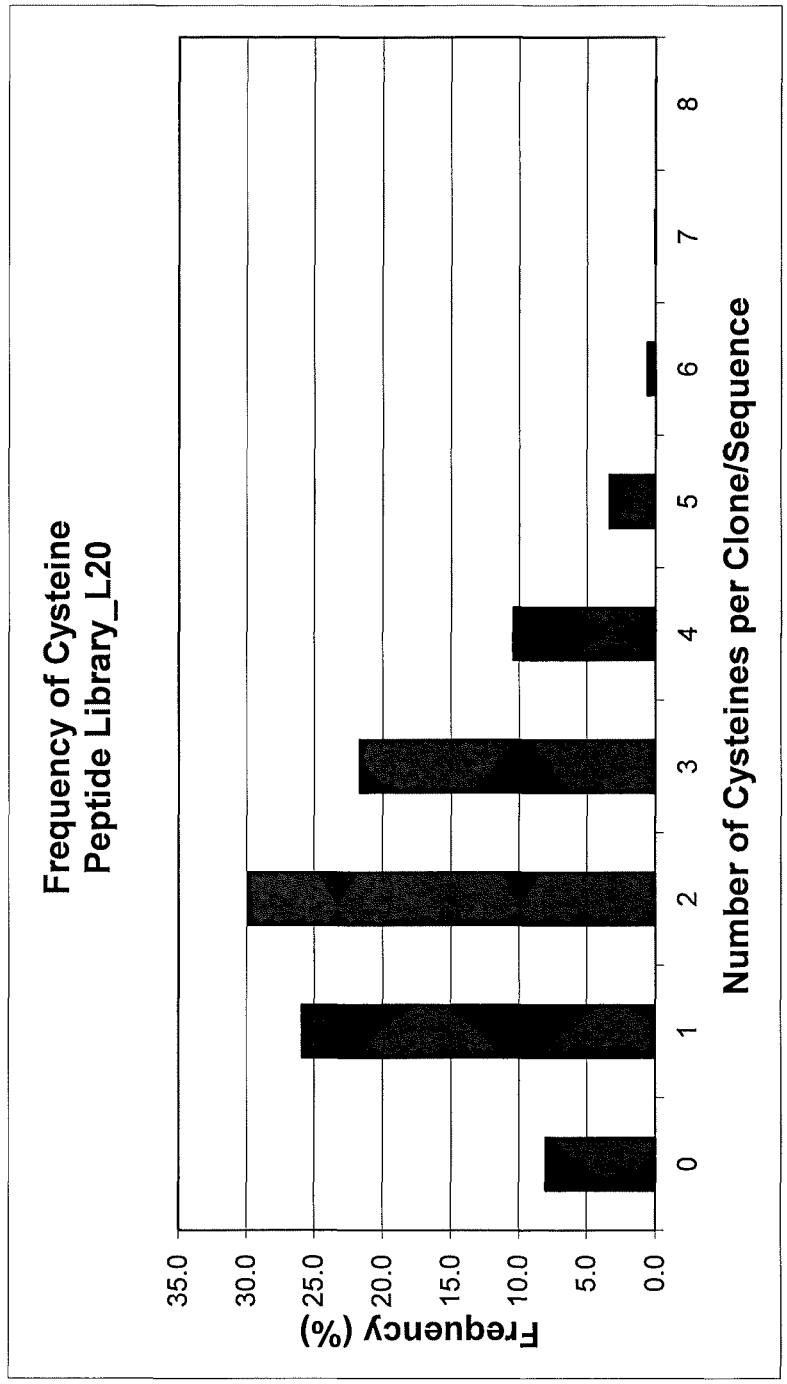
Figure 3C:
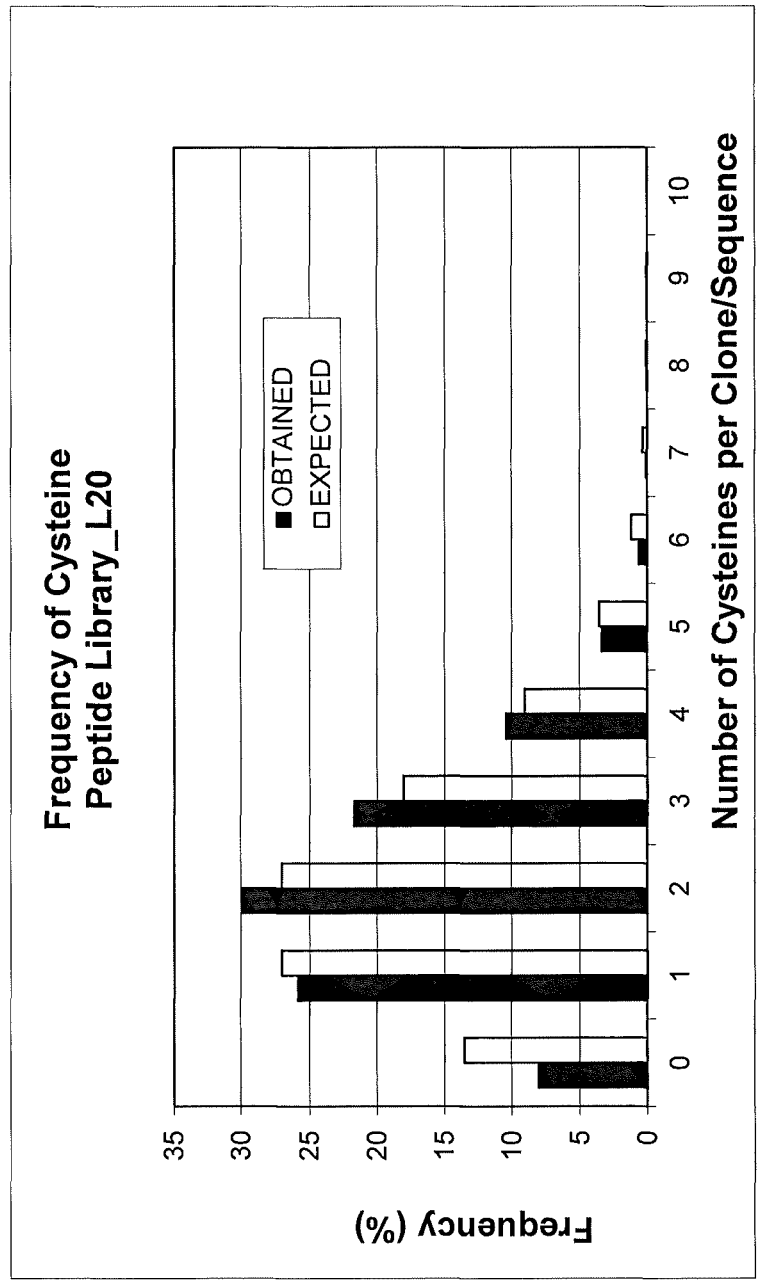

Of the 99 individual clones sampled from the library of FIG. 1, on average, 2.27 cysteines were identified per clone. In addition, clones were shown to have 0, 1, 2 or more cysteines, and of the clones sampled 33% were linear and 67% were cyclic, see FIGS. 3A-3C. Of the 99 individual clones sampled from the library of FIG. 1, 67% were cyclic peptides. The cyclic peptides comprised loops ranging in size from 3-17 amino acids in length, see FIGS. 4A-B. FIGS. 5-6 show example peptides that result from the library of FIG. 1, which have at least two disulfide bonds, and may result in various sized loops within one peptide.

Of the 99 sampled peptides: 42 of the 99 had a cysteine at position 4, which allowed for the formation of a large loop. Of the 42 having a cysteine at position 4: 16 had a total of 2 Cys forming one large loop; 18 of the 42 had 3 cysteines forming either one large or one small loop; 3 of the 42 had 4 cysteines forming one large and one small loop; 1 of the 42 had 5 cysteines, 1 of the 42 had 6 cysteines, 1 of the 42 had 7 cysteines, each forming one large and several small loops. Of the 24 cyclic peptides having no cysteine at position 4, which therefore can only form small loops, 10 of the 24 had 2 cysteines forming one loop; 8 of the 24 had 3 cysteines forming one loop; 6 of the 24 had 4 cysteines and were able to form up to two loops; 1 of the 24 had 5 cysteines, and 1 of the 24 had 6 cysteines and were able to form multiple loops.

Example 5: Pannings

The suitability of the peptide libraries disclosed herein for epitope mapping, and for the identification of therapeutic peptides was analyzed using available model antigens and antibodies whose epitopes are known.

Both libraries (pIII and pVIII) were used for solid phase and solution pannings with Streptavidin and the anti c-Myc antibody. Streptavidin was obtained from IBA (Goettingen, Germany). The anti-cMyc mouse mAb was obtained from Santa Cruz Biotechnology (Heidelberg, Germany).

Test selection with disulfide-constrained peptide libraries pIII (L20) and pVIII (L20) against Streptavidin beads and anti c-Myc antibody.

Streptavidin was used as antigen for test panning because the binding consensus motif HPQ/M is well described and used in several studies for test selection of peptide libraries (Devlin, J. J., Panganiban, L. C. and Devlin, P. E. (1990) Science 249, 404-406; Lam, K. S. and Lebl, M: Streptavidin and Avidin Recognize Peptide Ligands with Different Motifs. Immuno Methods 1: 11-15, 1992).

Here both peptide libraries were handled according to published standard protocols for phage display based peptide selections (Zwick, M. B., Menendez, A., Bonnycastle, L. L. C. and Scott, J. K. (2001). In C. F. Barbas, D. R. Burton, J. K. Scott and G. J. Silverman, (Eds.), *Phage Display: A Laboratory Manual* (pp. 18.1-18.44). New York: Cold Spring Harbor Laboratory Press;) with minor adjustments in terms of selection stringency and adaptation to phagemide vector system. The test selections were performed over 3 subsequent enrichment rounds with monitoring of specific sequences by conventional and next generation sequencing. In short, all pannings were completed with various antigen concentrations (100 nM for round 1, 50 nM for round 2, and 25 nM for round 3) under standard and less stringent washing conditions. After incubation of the phage with antigens, unspecific bound phages were washed off using PBST and subsequently, the specifically bound phage were eluted using Glycine/HCl.

For solid phase pannings the target proteins (Streptavidin and anti-cMyc mIgG) were diluted in PBS for direct coating the surface of a microtiter plate with a protein concentration of 100 nM. For each sublibrary 2 wells of a microtiter plate were coated with the target proteins using 300 μl protein solution per well. The plate was stored overnight at 4° C. Then the protein solution was removed from the coated wells by rapidly inverting the plate over a plastic tray. The coated wells were washed twice with 400 μl PBS and blocked with 400 μl blocking buffer for 2 h at RT on a microtiter plate shaker.

Meanwhile the phage blocking mixtures were incubated in 2 ml reaction tubes for 2 h at RT shaking gently. After the blocking procedure the wells were washed 2 times with 400 μl PBS and the 300 μl of the pre-blocked phage mix transferred into each blocked well. It was incubated for 2 h at RT on a microtiter plate shaker. After that the phage solution from the target protein coated wells were removed by rapidly inverting the plate over a plastic tray and plates were washed with the following washing conditions (Table 1 and 2).

TABLE 1

| (Standard washing conditions) | | |
|---|---|---|
| 1 st round | 2nd round | 3rd round |
| 3x PBST quick | 1x PBST quick | 10x PBST quick |
| 2x PBST for 5 min | 4x PBST for 5 min | 5x PBST for 5 min |
| 3x PBS quick | 1x PBS quick | 10x PBS quick |
| 2x PBS for 5 min | 4x PBS for 5 min | 5x PBS for 5 min |

TABLE 2

| (Less stringent washing conditions) | | |
|---|---|---|
| 1 st round | 2nd round | 3rd round |
| 5x PBST quick | 4x PBST quick | 5x PBST quick |
| 5x PBS quick | 1x PBST for 5 min | 3x PBST for 5 min |
| | 4x PBS quick | 5x PBS quick |
| | 1x PBS for 5 min | 3x PBS for 5 min |

All washing steps were done at RT. After the washing steps all traces of the wash solution were removed by carefully tapping the microtiter plate on a new stack of paper towels. For the elution of specifically bound phage, 300 µl 100 mM Glycine/HCl, pH 2.2, 1 mg/ml BSA were added to each selection well and incubated at room temperature for 10-15 min without shaking. The eluates of each selection were collected and immediately neutralized with 40p1 1M Tris pH 8.

For bead based pannings Streptavindin-coated Dynabeads M280 (Invitrogen) or for binding of the anit-cMyc-antibody, Dynabeads-ProteinG (Life Technologies) were used. After blocking and washing of the beads the target proteins were incubated with pre-adsorbed phage. Washing of the coated magnetic Dynabeads was carried out with a magnetic particle separator and incubations were done by over head rotation in low binding tubes. Washing and elution conditions for the bead based solution pannings were identical to the solid phase pannings listed above (Table 1 and Table 2).

*E. coli* TG1F' with an OD600 nm of 0.6-0.8 was added to the phage eluates of each selection and was incubated in an incubator without shaking. After infection bacteria were plated out evenly on two large LB/Chloramphenicol/Glucose agar plates for each selection and incubated overnight at 37° C. and Glycerol phage stocks were prepared.

For the following panning rounds bacterial suspensions of each pool were collected and used to propagate phages for an additional panning round as described above.

After each round of panning the phage titer was determined. The expected range goes from $1\times10^{10}$-$1\times10^{12}$ phage/ml for the input and $10^4$-$10^9$ phage/ml for the output. Table 3 shows the input and the output after each round of panning and all values are in the expected range.

TABLE 3

| Sub-Library | Panning Strategy | Washing condition | Target | Phage Input 1st rd. | Phage Output 1st rd. | Phage Input 2nd rd. | Phage Output 2nd rd. | Phage Input 3rd rd. | Phage Output 3rd rd. |
|---|---|---|---|---|---|---|---|---|---|
| L20-pIII | Solid Phase | less stringent washing | Streptavidin | 9.0E+11 | 6.0E+05 | 1.7E+13 | 1.9E+06 | 2.3E+12 | 2.3E+07 |
| L20-pVIII | | | | 2.4E+11 | 6.0E+06 | 9.2E+13 | 1.9E+07 | 2.1E+12 | 4.7E+08 |
| L20-pIII | | standard washing | | 9.0E+11 | 7.7E+05 | 1.8E+12 | 2.3E+06 | 1.1E+12 | 2.6E+08 |
| L20-pVIII | | | | 2.4E+11 | 2.8E+06 | 3.0E+12 | 5.6E+06 | 1.8E+12 | 1.1E+09 |
| L20-pIII | | less stringent washing | anti-cMyc mIgG | 9.0E+11 | 4.9E+06 | 1.9E+12 | 1.9E+05 | 1.5E+12 | 8.3E+04 |
| L20-pVIII | | | | 2.4E+11 | 9.5E+05 | 4.5E+11 | 1.7E+06 | 2.2E+12 | 1.1E+07 |
| L20-pIII | | standard washing | | 9.0E+11 | 9.1E+04 | 1.7E+12 | 6.1E+04 | 2.9E+12 | 6.1E+04 |
| L20-pVIII | | | | 2.4E+11 | 5.6E+05 | 1.5E+12 | 2.3E+06 | 1.8E+12 | 6.4E+05 |
| L20-pIII | Solution Phase | less stringent washing | Streptavidin-Beads (Dynabeads SA M-280) | 6.0E+12 | 1.1E+07 | 6.0E+11 | 9.4E+06 | 1.1E+12 | 2.2E+09 |
| L20-pVIII | | | | 1.6E+12 | 3.1E+07 | 7.8E+11 | 3.8E+09 | 9.6E+11 | 8.2E+09 |
| L20-pIII | | standard washing | | 6.0E+12 | 5.6E+07 | 6.6E+11 | 7.5E+06 | 4.8E+11 | 1.8E+09 |
| L20-pVIII | | | | 1.6E+12 | 2.6E+08 | 9.0E+11 | 1.2E+09 | 1.1E+12 | 2.7E+09 |
| L20-pIII | | less stringent washing | anti-cMyc mIgG-Beads (Dynabeads-ProteinG) | 6.0E+12 | 1.1E+07 | 1.8E+11 | 1.1E+08 | 9.0E+11 | 2.6E+09 |
| L20-pVIII | | | | 1.6E+12 | 2.4E+07 | 7.8E+11 | 5.9E+08 | 1.3E+12 | 1.9E+09 |
| L20-pIII | | standard washing | | 6.0E+12 | 5.6E+07 | 6.6E+11 | 5.6E+06 | 1.0E+12 | 1.2E+09 |
| L20-pVIII | | | | 1.6E+12 | 1.2E+07 | 9.6E+11 | 4.7E+08 | 1.3E+12 | 2.1E+09 |

After completion of the panning rounds phage output pools were analyzed with respect to their binding specificity in an additional differential panning round and ELISA against the specific and unrelated target proteins, such as VEGF-165. The check for specificity of binding by ELISA was carried out by using direct coated target proteins and peptide displaying phage from panning outputs. Bound phages were detected by the additionally encoded Flag tag using anti-Flag detection. To analyze phage expression anti-M13 capture and anti-Flag detection was used.

NGS analysis and ELISA of the phage outputs from subsequent and differential panning rounds revealed an enrichment of specific binders, that bound to the specific target proteins but did not show binding to unrelated target proteins. Primary hits were defined as an ELISA signal of at least 5-fold above the background.

Example 6: Results of Pannings

Results of Sequencing of Streptavidin Binders

Sanger Sequencing was completed on single clones from the panning outputs. A sample of the sequences identified from the Streptavidin binders are shown in FIG. 11. The known consensus motif, HPQ/M, binding to Streptavidin is clearly shown in both linear and cyclic peptides. In cyclic peptides the motifs were found in small and large rings. This confirms the utility of such a library and of the libraries' resultant peptides, as they are useful in accurately mapping the epitope of binding molecules and/or the region of interest on antigens.

Example 7: Results of Sequencing of c-Myc Binders

Selections against an anti-c-Myc antibody were completed as described above in Example 5 using the library described in Example 3.

Figure 12:
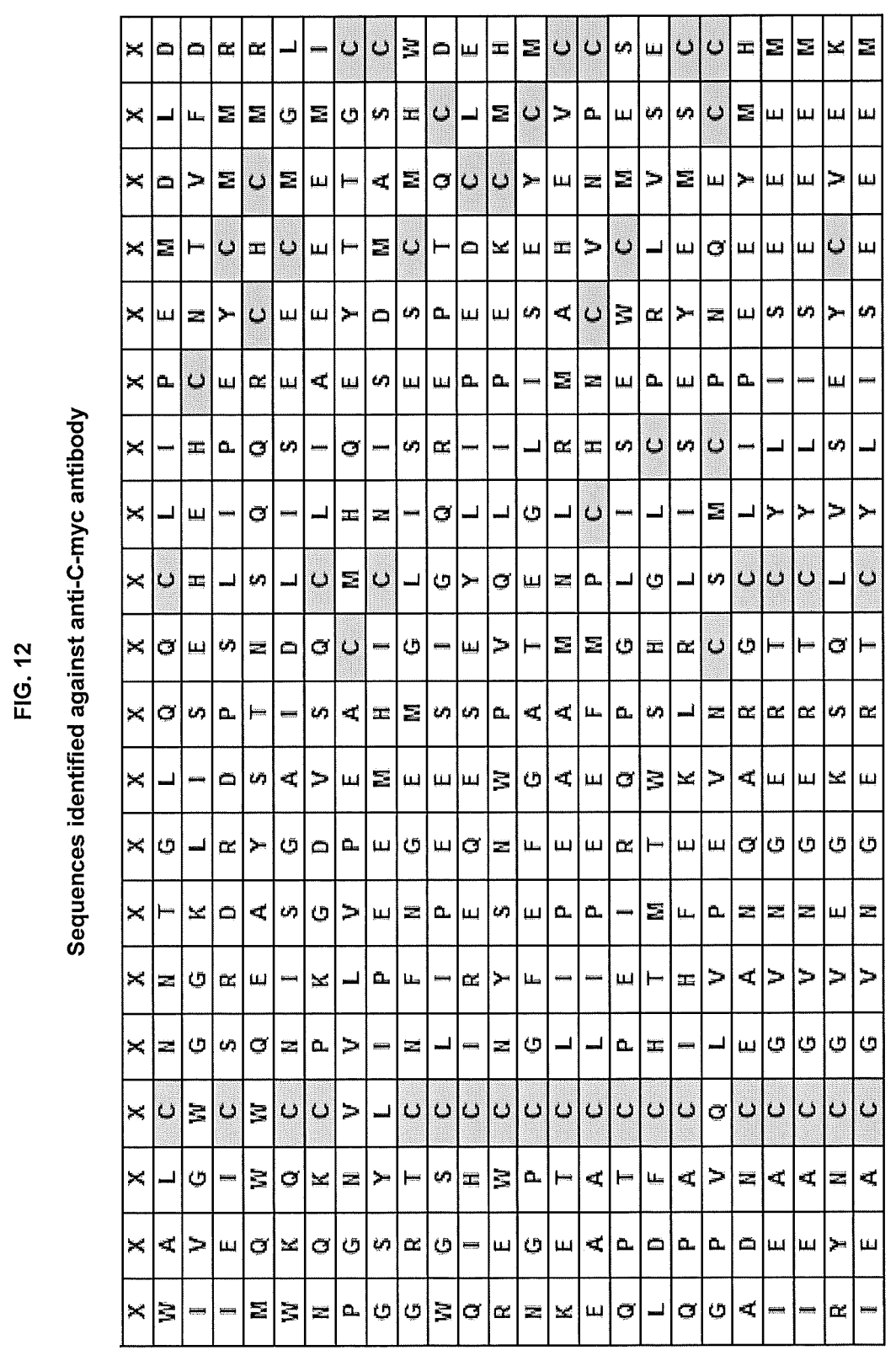

Sanger Sequencing was completed on single clones from the panning outputs. A sample of the sequences identified from the Streptavidin binders are shown in FIG. 12. This result confirms that a diverse number of specific peptides were identified, wherein the peptides selected are both linear, constrained, and have a wide range of confirmations, and loop lengths.

In early selection rounds it is desirable to identify a wide range of different peptide conformations that are specific for the antigen of interest, here c-myc. As a next step, the identified peptides could be characterized for their functional properties, such as, affinity, function in relevant assay, etc. A person of skill in the art would immediately realize that this library could be used in the discovery phase to identify potential therapeutically relevant peptides that could be developed for pharmaceutical use.

The invention claimed is:

1. A library of synthetic peptides, comprising linear and cyclic peptides,
   wherein the cyclic peptides have different loop lengths, and
   wherein some of the cyclic peptides have single loops and other cyclic peptides have two or more loops, and
   wherein the synthetic peptides of said library comprise a controlled ratio of cysteines at certain positions,
   wherein the cyclic peptides are formed by one or more covalent bonds,
   wherein said covalent bond is a disulfide bond formed by two cysteine residues,
   wherein synthetic peptides of the library comprise an amino acid sequence Cmix-(X)m-(Amix)n, wherein
   a) Cmix is a mixture of 50% cysteine or an equal mixture of remaining natural occurring amino acids excluding cysteine,
   b) X are each an equal mixture of natural occurring amino acids, excluding cysteine,
   c) Amix are each a mixture of 5-50% cysteine or an equal mixture of remaining natural occurring amino acids, and
   d) m and n are both, and independently from each other, 3-20.

2. The library of claim 1, wherein the loop lengths range from 3-17 amino acids in length.

3. The library of claim 1, wherein the synthetic peptides of said library are translated from nucleic acids.

4. The library of claim 1, wherein the synthetic peptides of said library are displayed on bacteriophage.

5. The library of claim 1, wherein each member of the library comprises an amino acid sequence Cmix-(X)m-(Amix)n, wherein
   a) Amix are each a mixture of 10-20% cysteine and an equal mixture of the remaining natural occurring amino acids,
   b) m is 5-6, and
   c) n is 3-20.

6. The library of claim 5, wherein each member of the library comprises an amino acid sequence (X)l-Cmix-(X)m-(Amix)n, wherein
   a) l is 1-3.

7. The library of claim 6, wherein each member of the library comprises an amino acid sequence (X)l-Cmix-(X)m-(Amix)n, wherein
   a) Amix are each a mixture of 15% cysteine and an equal mixture of the remaining natural occurring amino acids,
   b) l is 3,
   c) m is 6, and
   d) n is 10.

8. A library of nucleic acids encoding the library of peptides of claim 1.

9. A vector comprising the nucleic acids of claim 8.

10. The vector of claim 9, wherein said vector is a display vector or an expression vector.

11. A method of identifying a peptide specific for an antigen, comprising
   (a) contacting an antigen with a library of claim 1, and
   (b) selecting one or more peptides specific for said antigen.

* * * * *